(12) United States Patent
Itsuji

(10) Patent No.: US 8,759,769 B2
(45) Date of Patent: Jun. 24, 2014

(54) TERAHERTZ-WAVE DEVICE, METHOD OF GENERATING AND DETECTING TERAHERTZ-WAVES WITH THE DEVICE, AND IMAGING APPARATUS EQUIPPED WITH THE DEVICE

(75) Inventor: Takeaki Itsuji, Hiratsuka-shi (JP)

(73) Assignee: Canon Kabushiki Kaisha, Tokyo (JP)

( * ) Notice: Subject to any disclaimer, the term of this patent is extended or adjusted under 35 U.S.C. 154(b) by 506 days.

(21) Appl. No.: 13/196,134

(22) Filed: Aug. 2, 2011

(65) Prior Publication Data

US 2012/0032081 A1 Feb. 9, 2012

(30) Foreign Application Priority Data

Aug. 5, 2010 (JP) .................................. 2010-175826
Jul. 8, 2011 (JP) .................................. 2011-152377

(51) Int. Cl.
*G01N 21/35* (2014.01)

(52) U.S. Cl.
CPC ........ *G01N 21/3581* (2013.01); *G01N 21/3586* (2013.01)
USPC ...................... 250/338.1; 250/504 R; 250/340

(58) Field of Classification Search
CPC ........ G01J 3/108; G01J 3/42; G01N 21/3586; G01N 21/3581; G02F 2203/13; G02F 1/35
USPC .................................... 250/340, 338.1, 504 R
See application file for complete search history.

(56) References Cited

U.S. PATENT DOCUMENTS

| | | | |
|---|---|---|---|
| 2002/0074500 A1* | 6/2002 | Mickan et al. | 250/341.8 |
| 2010/0258727 A1* | 10/2010 | Itsuji et al. | 250/338.4 |
| 2012/0032080 A1* | 2/2012 | Koyama et al. | 250/339.07 |
| 2012/0049072 A1* | 3/2012 | Kajiki et al. | 250/351 |
| 2013/0037721 A1* | 2/2013 | Ouchi | 250/353 |
| 2013/0240740 A1* | 9/2013 | Ouchi | 250/353 |
| 2013/0284950 A1* | 10/2013 | Shiota et al. | 250/504 R |

OTHER PUBLICATIONS

Hebling et al., Generation of high-power terahertz pulses by tilted-pulse-front excitation and their application possibilities, Journal of Optical Society of America, Jul. 2008, pp. B6-B19, vol. 25, No. 7.

* cited by examiner

*Primary Examiner* — David Porta
*Assistant Examiner* — Gisselle Gutierrez
(74) *Attorney, Agent, or Firm* — Canon USA Inc. IP Division

(57) ABSTRACT

A terahertz-wave generating device including an optical waveguide containing an electrooptic crystal includes: first and second optical waveguides through which first and second light beams respectively propagate; a propagation portion through which a first terahertz wave propagates, the first terahertz wave being generated from the second optical waveguide in a direction different from a direction of the second light beam; and a delay portion arranged at incidence sides of the first and second light beams and configured to delay the first light beam relative to the second light beam. The first optical waveguide and the second optical waveguide are arranged with the propagation portion interposed therebetween. A first equiphase surface of the first terahertz wave is substantially aligned with a second equiphase surface of a second terahertz wave generated from the first optical waveguide in a direction different from a direction of the first light beam.

20 Claims, 8 Drawing Sheets

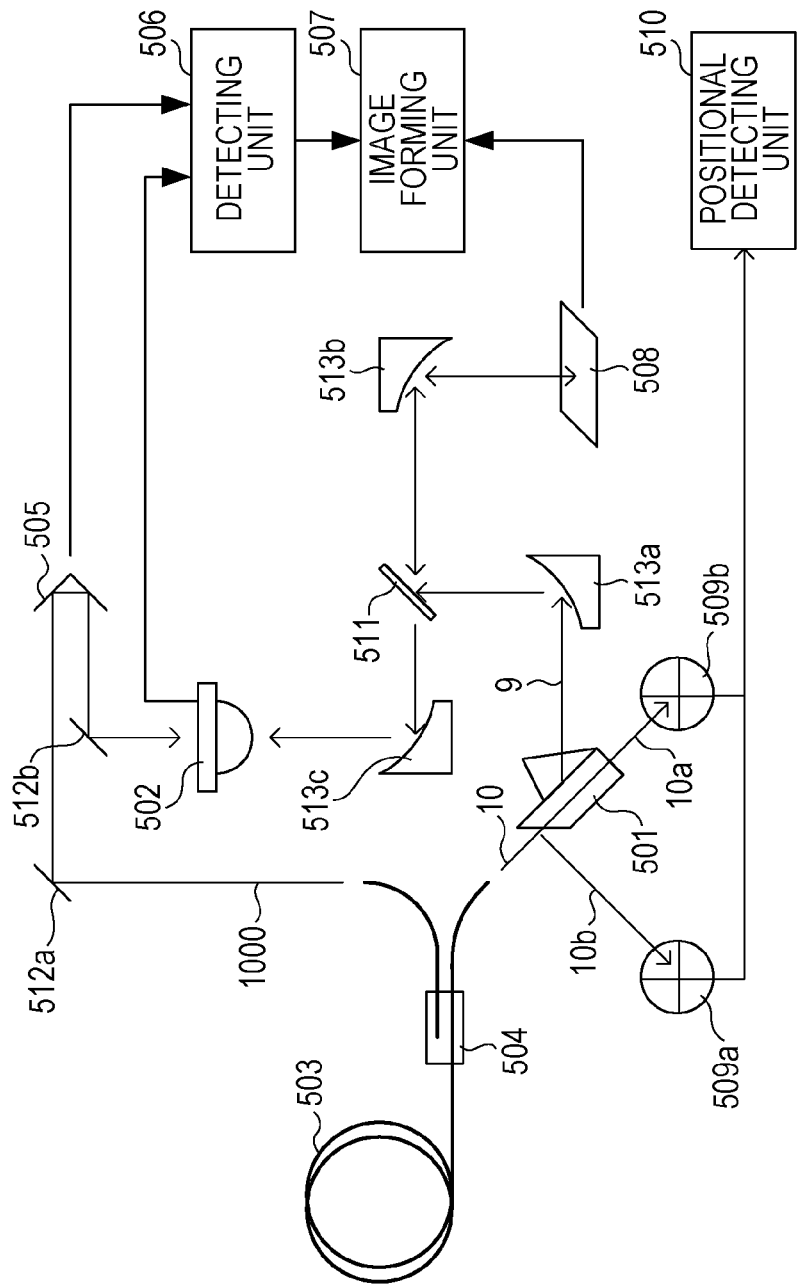

TERAHERTZ-WAVE DEVICE, METHOD OF GENERATING AND DETECTING TERAHERTZ-WAVES WITH THE DEVICE, AND IMAGING APPARATUS EQUIPPED WITH THE DEVICE

BACKGROUND OF THE INVENTION

1. Field of the Invention

The present invention relates to elements and devices configured to generate and detect terahertz waves, methods of generating and detecting terahertz waves, and a measuring device using a terahertz time-domain spectroscopic system.

2. Description of the Related Art

Terahertz (THz) waves are electromagnetic waves containing components in any frequency band from approximately 0.03 to 30 THz. Many characteristic absorptions originating from structures and states of various substances such as biomolecules are present in such a frequency band. By using the characteristic, an inspection technique that analyzes or identifies substances in a non-destructive manner has been developed. Also, application to a safe imaging technique by using terahertz waves instead of X-rays and application to a high-speed communication technique have been proposed. A method of generating terahertz waves includes using a nonlinear optical crystal to generate second order nonlinear optical effects (difference frequency generation). Representative nonlinear optical crystals include $LiNbO_x$ (Lithium Niobate or simply "LN"), $LiTaO_x$, $NbTaO_x$, KTP, DAST, ZnTe, GaSe, and the like. Generation of terahertz waves uses the second-order nonlinear properties of these crystals, upon which two laser beams with a frequency difference are incident. Specifically, in nonlinear crystal materials, difference frequency generation (DFG) can occur where two laser beams generate another beam with the difference of the optical frequencies of the two laser beams. Also, generation of single-color terahertz waves through an optical parametric process, and an optical rectification method by irradiation of femtosecond pulsed laser beams have been known.

As a process of generating terahertz waves from such a nonlinear optical crystal, electrooptic Cerenkov radiation has received attention lately. This phenomenon occurs if a propagation group velocity of laser beams propagating through the nonlinear optical crystal is higher than a propagation phase velocity of generated terahertz waves. In such a situation, the terahertz waves are radiated in a conical form within the nonlinear optical crystal like shock waves. This is a method of generating terahertz waves by excitation of progressive waves. Hence, by matching phases of terahertz waves generated from different wave sources in a radiation direction, the intensity of terahertz waves can be increased. For example, there is a report that, when a femtosecond laser beam with its wavefront inclined is incident on LN, phase matching is provided in a radiation direction of terahertz waves. See, Hebling et at., "Generation of high-power terahertz pulses by tilted-pulse-front excitation and their application possibilities," J. Opt. Soc. Am. B, vol. 25, pp. B6-B19, (2008). (Hereinafter, referred to as document 1).

In the method described in document 1, to satisfy a phase matching condition, the wavefront of the laser beam is optically inclined and is aligned with the radiation direction of the terahertz waves. However, alignment is difficult for an optical system that adjusts the shape of the wavefront of the light beam. Hence, a system utilizing this method can be cumbersome and complicated. Also, in the method of the document 1, a nonlinear crystal bulk is used. Such a nonlinear crystal has a large loss for the terahertz waves. Hence, it is difficult to radiate terahertz waves with high output radiation.

SUMMARY OF THE INVENTION

According to an aspect of the present invention, a terahertz-wave generating device including an optical waveguide containing an electrooptic crystal includes: a first optical waveguide through which a first light beam propagates; a second optical waveguide through which a second light beam propagates; a propagation portion through which a first terahertz wave propagates, the first terahertz wave being generated from the second optical waveguide in a direction different from a direction of the second light beam; and a delay portion arranged at incidence sides of the first and second light beams and configured to delay the first light beam relative to the second light beam. The first optical waveguide and the second optical waveguide are arranged with the propagation portion interposed therebetween. A first equiphase surface of the first terahertz wave is substantially aligned with a second equiphase surface of a second terahertz wave that is generated from the first optical waveguide in a direction different from a direction of the first light beam.

With the terahertz-wave generating device according to the aspect of the present invention, the equiphase surfaces of the terahertz waves generated from the plurality of positions can be substantially aligned with each other and the terahertz waves can be extracted. Accordingly, the terahertz waves with relatively high intensities can be generated.

Further features of the present invention will become apparent from the following description of exemplary embodiments with reference to the attached drawings.

BRIEF DESCRIPTION OF THE DRAWINGS

FIG. 5 is an illustration explaining an imaging apparatus using the terahertz-wave generating device according to the embodiment of the present invention.

DESCRIPTION OF THE EMBODIMENTS

The present invention has a feature in which, by delaying a first excitation light beam (first light beam) relative to a second excitation light beam (second light beam), and by consuming a time before a first terahertz wave reaches a generation position from a second optical waveguide, first and second equiphase surfaces of first and second terahertz waves are substantially aligned with each other. Also, terahertz waves can be detected by the same configuration in a reverse process. An electrooptic crystal used here for a first-order electrooptic effect has a second-order nonlinear characteristic. An electrooptic crystal, which is typically practically usable, is substantially equivalent to a nonlinear optical crystal having a second-order nonlinear property. Based on this idea, devices, elements, and methods configured to generate and detect terahertz waves have basic configurations described in the Summary.

Embodiments and examples of the present invention will be described below with reference to the drawings.

First Embodiment

Figure 1A:
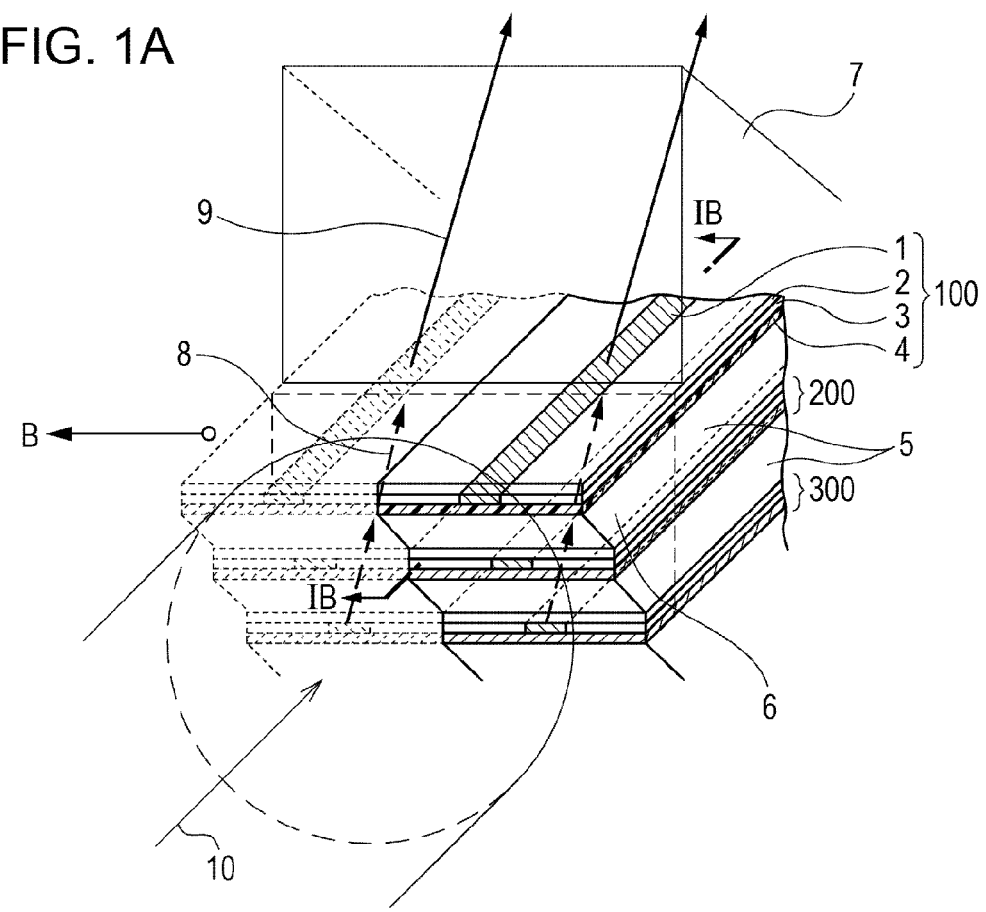
FIG. 1A is a perspective view explaining a terahertz-wave generating element according to an embodiment and an example of the present invention.
Figure 1B:
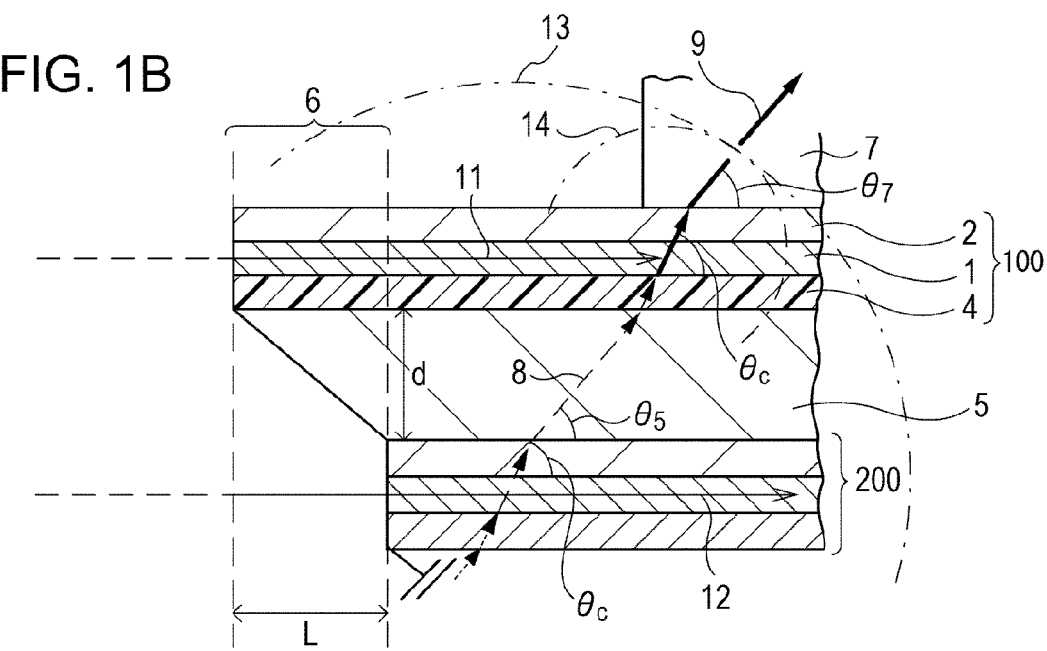
FIG. 1B is a cross-sectional view explaining the terahertz-wave generating element according to the embodiment and the example of the present invention.

A first embodiment of the present invention for terahertz-wave generating element and device etc. will be described. FIGS. 1A and 1B illustrate a terahertz-wave generating element formed of a nonlinear optical crystal which is an electrooptic crystal. FIG. 1A is a perspective view of the terahertz-wave generating element. FIG. 1B is a cross-sectional view of the terahertz-wave generating element taken along line IB-IB. The terahertz-wave generating element of this embodiment is an element that generates a pulsed wave.

The terahertz-wave generating element shown in FIGS. 1A and 1B includes a first optical waveguide 100, a second optical waveguide 200, and a third optical waveguide 300 arranged with propagation portions 5 interposed among the waveguides 100 to 300. In the following description, since the principle of an element including three or more optical waveguides is the same as the principle of an element including two optical waveguides, an element including the first optical waveguide 100 and the second optical waveguide 200 is described. The first optical waveguide 100 and the second optical waveguide 200 use part of a laser beam 10 as a first excitation light beam 11 and a second excitation light beam 12 for generation of terahertz waves. A terahertz wave is generated by electrooptic Cerenkov radiation that is a second-order nonlinear phenomenon occurring in a LN crystal that forms part of an optical waveguide. A radiation angle $\theta_c$ of a terahertz wave with respect to a propagation direction of an excitation light beam can be evaluated with the following Expression (1):

$$\cos \theta_c = v_{THz}/v_g = n_g/n_{THz} \quad (1)$$

where $v_g$ is a group velocity of the excitation light beam, $n_g$ is a group refractive index for the excitation light beam, $v_{THz}$ is a phase velocity of the terahertz wave in the crystal, and $n_{THz}$ is a refractive index for the terahertz wave in the crystal. The electrooptic Cerenkov radiation is a phenomenon occurring if the group velocity of an excitation light beam propagating through an optical waveguide is higher than the phase velocity of a terahertz wave propagating through the optical path. Under such conditions, the generated terahertz wave is radiated in a conical form like a shock wave.

In this embodiment, the first optical waveguide 100 has the same structure as the second optical waveguide 200. Referring to FIGS. 1A and 1B, the first optical waveguide 100 includes a core portion 1, a first cladding portion 2, a second cladding portion 3, and a third cladding portion 4. The first cladding portion 2 and the third cladding portion 4 face each other with the core portion 1 interposed therebetween. The second cladding portion 3 is arranged to fill a gap between the first cladding portion 2 and the third cladding portion 4 at a side surface of the core portion 1. That is, the core portion 1 is surrounded by the first cladding portion 2, the second cladding portion 3, and the third cladding portion 4. The core portion 1 has a refractive index higher than refractive indices of the respective cladding portions for the first excitation light beam 11 that is included in the laser beam 10 and is incident on the first optical waveguide 100. Accordingly, an optical waveguide is formed by the core portion 1 such that the first excitation light beam 11, which is incident on the first optical waveguide 100, is enclosed in the core portion 1 and propagates through the core portion 1.

A required thickness of the core portion 1 is a half or smaller of an equivalent wavelength in an element equivalent to a maximum frequency of a terahertz wave desired to be extracted from an optical waveguide. Determining the thickness in this way prevents that the phases of terahertz waves generated at an interface between the core portion 1 and the first cladding portion 2 and at an interface between the core portion 1 and the third cladding portion 4 are reversed and canceled with each other. Thicknesses of the first cladding portion 2 and the third cladding portion 4 are desirably sufficiently large so as to function as cladding regions for the first excitation light beam 11 propagating through the core portion 1. Also, thicknesses of the respective cladding portions are desirably small so that influences of multiple reflection and a loss of the terahertz waves are negligible. For example, the thicknesses are determined so that a light intensity distribution of a light beam, which propagates through the core portion 1 and enters the respective cladding portions, is $1/e^2$ or smaller of a light intensity of the first excitation light beam 11 in the core portion 1. Also, the thicknesses of the respective cladding portions are desirably determined to a thickness from about $(1/10)\lambda$ to $(1/20)\lambda$ with respect to an equivalent wavelength $\lambda$ of a terahertz wave in an element with a highest frequency from among frequencies of terahertz waves desired to be extracted. By determining the thicknesses in this way, the terahertz wave hardly recognizes the first cladding portion 2 and the third cladding portion 4 as structures. Consequently, it is expected that reflection, scattering, refraction of the terahertz wave can be negligible. However, the terahertz wave can be generated from the terahertz-wave generating element according to the embodiment of the present invention even if the thicknesses exceed the desirable thickness range.

The thickness of the second cladding portion 3 corresponds to the thickness of the core portion 1. Referring to FIG. 1A, a plurality of generating elements of this embodiment may be arranged in the direction of the normal to the longitudinal direction of the first optical waveguide 100 (in B direction) through the second cladding portion 3. At this time, the width of the second cladding portion 3 in the B direction is determined so that the light intensity distribution of the light beam, which enters the second cladding portion 3, is $1/e^2$ or smaller of the light intensity of the light beam in the core portion 1.

The core portion 1 is a nonlinear optical crystal, such as $LiNbO_x$ (LN), $LiTaO_x$, $NbTaO_x$, KTP, DAST, ZnTe, or GaSe. The first cladding portion 2, the second cladding portion 3, and the third cladding portion 4 use materials with refractive indices smaller than the refractive index of the core portion 1. For example, a resin material or a nonlinear optical crystal used for the core portion 1 may be used. If a nonlinear optical crystal is used as a clad, to have a refractive index different from the refractive index of the core portion 1, the core portion 1 is formed in a dope region by diffusion using metal such as titanium (Ti). Also, these clads also serve as adhesives. Alternatively, an adhesive region may be provided.

The propagation portion 5 allows a first terahertz wave 8 to propagate therethrough. The first terahertz wave 8 is generated from the second optical waveguide 200 and is generated in a direction different from the direction of the second excitation light beam 12. The propagation portion 5 relays the first terahertz wave 8 to the first optical waveguide 100. When a radiation angle of the terahertz wave in the second optical waveguide 200 is $\theta_c$, a radiation angle $\theta_5$ of the first terahertz wave propagating through the propagation portion 5 can be expressed as follows:

$$\cos\theta_5/\cos\theta_c = n_{THz}/n_5 \qquad (2),$$

where $n_5$ is a refractive index of the propagation portion 5 for the first terahertz wave 8, and $n_{THz}$ is a refractive index of the nonlinear optical crystal for the terahertz wave. As estimated from Expression 2, $n_5$ has to select a value such that the terahertz wave generated at the second optical waveguide 200 is not totally reflected by the interface between the second optical waveguide 200 and the propagation portion 5. Also, the material of the propagation portion 5 may be any as long as the material satisfies the refractive index $n_5$. A material with a small loss and a dispersion for the first terahertz wave 8 is desirably selected.

The thickness d of the propagation portion 5 is adjusted such that a first equiphase surface 13 of the first terahertz wave 8 is substantially aligned with a second equiphase surface 14 of the second terahertz wave 9. Similarly to the first terahertz wave 8, the second terahertz wave 9 is generated from the first optical waveguide 100 and is generated in a direction different from the direction of the first excitation light beam 11. In this specification, being "substantially aligned" includes being "completely aligned" and being "shifted by an amount within an allowable range" (being "substantially equivalent" is also defined similarly). Being completely aligned is more desirable; however, as long as the aligned state increases the intensities of the first and second terahertz waves, the first and second equiphase surfaces may be shifted from each other. The allowable range varies depending on a condition required for the element. For example, if slight intensity beat or intensity degradation is allowable, the phases may be shifted by a certain degree from the completely aligned state. Of course, a situation in which phases are shifted by about 180 degrees and intensities are markedly degraded should be eliminated. In the case of this embodiment, the upper limit of the thickness d of the propagation portion 5 is desirably determined such that a beam diameter of the laser beam 10 incident on the terahertz-wave generating element accommodates at least a single pair of the first optical waveguide 100 and the second optical waveguide 200. In other words, the beam diameter of the laser beam 10 may be adjusted to satisfy the above condition. With this value, the first excitation light beam 11 and the second excitation light beam 12 can be introduced into the first optical waveguide 100 and the second optical waveguide 200. Also, the lower limit of the thickness d of the propagation portion 5 is determined such that an interval between the core portions that form the respective optical waveguides satisfies the following condition. In particular, when $\lambda$ is an equivalent wavelength when a wavelength component with a highest frequency propagates between the core portions, from among frequency components of the terahertz waves desired to be extracted, the interval between the core portions is desirably determined to be equal to or larger than a thickness from about $(1/10)\lambda$ to $(1/20)\lambda$. With this value, the terahertz waves can recognize the structures of the optical waveguides, and hence the first optical waveguide 100 and the second optical waveguide 200 can be optically separated from each other.

A delay portion 6 is provided at the input stage of the laser beam 10 that is incident on the respective optical waveguides. The delay portion 6 delays a timing at which the first excitation light beam 11 reaches the output side of the delay portion 6, relative to the second excitation light beam 12, which is part of the laser beam 10. FIGS. 1A and 1B illustrate an example in which the delay portion 6, the respective optical waveguides, and the propagation portion 5 are bonded together as an integrated element. Alternatively, the delay portion 6 may be separated. Still alternatively, two delay portions 6 may be provided, and one may be separated and the other may be bonded with the respective optical waveguides and the propagation portion 5. In this way, the terahertz-wave generating element may be configured as a terahertz-wave generating device.

As shown in FIGS. 1A and 1B, in this embodiment, end surfaces of the first optical waveguide 100 and second optical waveguide 200, which are arranged with the propagation portion 5 interposed therebetween, are shifted from each other at the incidence side of the laser beam 10. Specifically, there is a structure in which the position of the end surface of the second optical waveguide 200 at the incidence side of the second excitation light beam 12 is shifted from the position of the end surface of the first optical waveguide 100 at the incidence side of the first excitation light beam 11, by a predetermined distance L in a propagation direction of the second excitation light beam 12. In the element of this embodiment, a region having this structure is named delay portion 6. Accordingly, the delay portion 6 is positioned (arranged) at a side of one of the optical waveguides, on which side one of the excitation light beams is incident. Put another way, in FIG. 1B, the delay portion 6 is arranged at a side of the optical waveguide 100 where the excitation light beam 11 is incident. However, the delay portion 6 can alternatively be arranged at the side of the optical waveguide 200 where the excitation light beam 12 is incident.

In this embodiment, the delay portion 6 delays a time in which the first excitation light beam 11 propagates through the terahertz-wave generating element relative to the second excitation light beam 12. In the delay portion 6, the first excitation light beam 11 propagates through the first optical waveguide 100 whereas the second excitation light beam 12 propagates through free space. Consequently, physical constants of the paths in which the excitation light beams respectively propagate differ from each other. Hence, in the delay portion 6, a propagation velocity of the first excitation light beam 11 is different from the propagation velocity of the second excitation light beam in free space. By using the difference between the propagation velocities of the excitation light beams, the delay portion 6 can delay the first excitation light beam 11 relative to the second excitation light beam 12. By providing the delay portion 6, generation timings of the first terahertz wave 8 generated from the second optical waveguide 200 and the second terahertz wave 9 generated from the first optical waveguide 100 can be adjusted.

In particular, in this embodiment, the timing at which the first terahertz wave 8 is generated at a position at which the second terahertz wave 9 is generated in the first optical waveguide 100 is adjusted. The delay portion 6 adjusts the excitation light beams such that a time at which the first terahertz wave 8 reaches the generation position is substantially aligned with a time at which the second terahertz wave 9 is generated at the generation position. Consequently, the first equiphase surface 13 of the first terahertz wave 8 is substantially aligned with the second equiphase surface 14 of the second terahertz wave 9. Accordingly, the intensities of the first terahertz wave 8 and second terahertz wave 9 can be increased.

In this embodiment, the distance L that defines the delay portion 6 is obtained by an expression as follows:

$$L = \tan\theta_5 \times d \qquad (3),$$

where $\theta_5$ is a radiation angle of the first terahertz wave 8 that propagates through the propagation portion 5, and d is a thickness of the propagation portion 5. When materials of respective portions that form the terahertz-wave generating element are determined, in this embodiment, the equiphase surfaces of the respective terahertz waves are adjusted by the thickness d of the propagation portion 5 and the distance L of the delay portion 6, so that the terahertz waves are substantially aligned. In the above description, in the delay portion 6, the second excitation light beam 12 propagates through the space; however, it is not limited thereto. Since this embodiment uses the difference between the propagation velocities of the excitation light beams, for example, a substance having a refractive index lower than a refractive index of the core portion 1 that forms the first optical waveguide 100 may be used for a propagation path of the second excitation light beam 12 in the delay portion 6.

FIG. 1A illustrates an example in which the three optical waveguides are arranged in the propagation direction of the terahertz wave, as the terahertz-wave generating element of this embodiment. Also, to extract the generated terahertz wave, an optical coupling member 7 is included. The optical coupling member 7 may be a prism, a diffraction grating, or a photonic crystal. As described above, by arranging a plurality of optical waveguides to meet the phase matching condition of a plurality of terahertz waves, the intensities of the terahertz waves can be increased.

This embodiment may have a configuration in which adjustment for the wavefront shape of a laser beam, the adjustment which has been performed to satisfy the phase condition, is performed at an end surface of the generating element. Specifically, timings at which the first excitation light beam 11 and the second excitation light beam 12 are incident are adjusted to satisfy the phase matching condition of a plurality of terahertz waves by the shapes of the first optical waveguide 100 and the second optical waveguide 200. Hence, when an apparatus form using the generating element of this embodiment is considered, an optical system, which has been required for inclining the wavefront of a laser beam, is no longer required, and the size of the apparatus can be decreased. Also, the shape of the wavefront of the laser beam does not have to be adjusted. A process such as alignment can be omitted, and workability is improved.

In the apparatus using the generating element of this embodiment, the first optical waveguide 100 and the second optical waveguide 200 are arranged with the propagation portion 5 interposed therebetween. Also, the equiphase surfaces of the terahertz waves generated from the optical waveguides are substantially aligned with each other. With this configuration, the propagation portion 5 can use a material having a small loss for the terahertz wave, and hence an apparatus with an increased intensity of the terahertz wave can be provided. Also, in the element of this embodiment, as described above, the timings at which the excitation light beams are incident on the core portion 1 of the optical waveguide are adjusted by the shapes of the first optical waveguide 100 and second optical waveguide 200. Accordingly, a laser beam with its wavefront shape adjusted does not have to be used as an excitation light beam, and the terahertz-wave generating element can become easily handled. Also, the propagation path of the first terahertz wave 8 generated from the second optical waveguide 200 and the propagation path of the second terahertz wave 9 generated from the first optical waveguide 100 can be linearly aligned. Hence, the intensity of the terahertz wave extracted from the element can be efficiently increased. That is, the core portions of the respective optical waveguides are substantially aligned with each other in the direction along the propagation path of the terahertz wave from the second optical waveguide to the first optical waveguide, and are arranged in parallel to the propagation direction of the excitation light beams. Accordingly, the intensity of the terahertz wave can be efficiently increased.

As described above, with the terahertz wave generation in this embodiment, the phase matching condition of the first terahertz wave 8 and the second terahertz wave 9 is satisfied by adjusting the timings at which the respective terahertz waves are generated. Consequently, the terahertz waves generated from the plurality of positions can be aligned with each other and extracted. The terahertz waves with high intensities can be generated.

EXAMPLE 1

Example 1 of the present invention will be described. This example is an example for an element and a device corresponding to the first embodiment. Here, description common to the description in the first embodiment will be omitted. In this example, as the laser beam 10, a pulse with a center wavelength of 1.55 µm, a pulse width of 20 femtoseconds, and a repetition frequency of 50 MHz is used. Also, a beam diameter is 1.56 mm. Alternatively, the wavelength may be 1.06 µm. Also, the pulse width and repetition frequency do not have to be the values described above. In this example, the laser beam 10 is a parallel light beam, and part of the light beam is used as the first excitation light beam 11 and the second excitation light beam 12.

The first optical waveguide 100 is configured as follows. The core portion 1 is LiNbO$_x$ doped in MgO. The core portion 1 has a thickness of 3.8 µm and a width of 5.0 µm. The first cladding portion 2 uses an optical adhesive with a thickness of 2.0 µm. The optical adhesive has a refractive index n of about 1.5. The second cladding portion 3 has the same thickness as the thickness of the core portion 1, and uses the same material as the material of the first cladding portion 2. The third cladding portion 4 has the same thickness as the thickness of the first cladding portion 2, and uses the same material as the material of the first cladding portion 2. That is, the first optical waveguide 100 is a ridge-shaped waveguide in which the core portion 1 is surrounded by the optical adhesives that are used as the second cladding portion 3, the third cladding portion 4, and the fourth cladding portion 5. The second optical waveguide 200 has the same configuration as that of the first optical waveguide 100.

A crystal used for the core portion 1 is a Y-cut crystal (the Y-axis of the crystal is parallel to a stacking direction of the optical waveguides). Regarding other crystal axes, the X-axis is a direction in which the excitation light beams propagate, and the Z-axis is a direction perpendicular to the stacking direction of the optical waveguides. However, the directions of the crystal axes are not limited thereto. For example, the core portion 1 may be arranged such that the Z-axis is parallel to the stacking direction of the respective optical waveguides. The laser beam 10 is incident on an element with in the form of a polarized wave so as to be parallel to the Z-axis. That is, polarized waves of the first excitation light beam 11 and the second excitation light beam 12 distributed from the laser beam 10 are parallel to the Z-axis. By using such polarized waves, the nonlinear effect of the nonlinear crystal can be maximally used, and generation efficiency of the terahertz waves extracted from the optical waveguides can be increased. However, the polarization direction with respect to the Z-axis is not limited thereto. For example, a phenomenon in which generation efficiency of a terahertz wave varies in accordance with a polarization direction may be used, and the intensity of the generated terahertz wave may be modified. In this case, a mechanism that relatively rotate the Z-axis of the core portion 1 and the polarization direction of the laser beam 10 is added.

The group refractive index ng of each optical waveguide for the excitation laser beam 10 is about 1.4. Also, the refractive index $n_{THz}$ for the terahertz wave is about 5.1. With Expression (1), the radiation angle $\theta_c$ of the terahertz wave with respect to the propagation direction of the excitation light beam is about 65.6 degrees. The propagation portion 5 uses semi-insulating high-resistance silicon. The thickness d of the propagation portion 5 is about 100 μm, and the refractive index $n_5$ for the terahertz wave is 3.2. The propagation portion 5 is bonded between the first optical waveguide 100 and the second optical waveguide 200 by an optical adhesive that is used as a clad. With Expression 2, the radiation angle $\theta_5$ of the first terahertz wave 8 that propagates through the propagation portion 5 is about 48.8 degrees.

The delay portion 6 is formed of the same material as the material of the propagation portion 5. As shown in FIG. 1B, the delay portion 6 in this example is a region in which the end surface of the first optical waveguide 100 is shifted from the end surface of the second optical waveguide 200 only by the distance L. With Expression 3, the distance L is about 114 μm. Also, in this example, the delay portion 6 is inclined with respect to the incidence direction of the laser beam 10 so as to connect the end surface of the first optical waveguide 100 with the end surface of the second optical waveguide 200 by the minimum distance. The inclination is provided to prevent vignetting from occurring for the first excitation light beam 11 and the second excitation light beam 12 that propagate through the optical waveguides, by an end portion of the delay portion 6. The structure of the end surface of the delay portion 6 is not limited thereto, and for example, the end surface may be a step-like shape or a curved surface.

The optical coupling member 7 is a prism, and uses the same material as the material of the propagation portion 5, i.e., semi-insulating high-resistance silicon. The optical coupling member 7 is held by an optical adhesive that is used as a cladding of the first optical waveguide 100. The optical coupling member 7 uses the same material as the material of the propagation portion 5. Thus, the radiation angle $\theta_7$ of the terahertz wave that propagates through the optical coupling member 7 is about 48.8 degrees.

As described above, the first optical waveguide 100 and the second optical waveguide 200 are arranged with the propagation portion 5 interposed therebetween. At this time, the core portions of the optical waveguides are arranged at positions at which the core portions are substantially aligned with each other in the direction of the propagation path of the terahertz wave from the second optical waveguide 200 to the first optical waveguide 100 (in the direction in which the optical waveguides are stacked). Further desirably, the core portions of the optical waveguides are arranged in parallel to the propagation direction of the excitation light beam. With such arrangement, the propagation path of the first terahertz wave 8 generated from the second optical waveguide 200 and the propagation path of the second terahertz wave 9 generated from the first optical waveguide 100 can be linearly aligned with each other. Accordingly, the intensities of the terahertz waves extracted from the element can be efficiently increased.

The operation of this example will be described. To simplify the description, an example using two optical waveguides is described. Of course, the number of optical waveguides to be used is not limited thereto. For example, as shown in FIG. 1A, three optical waveguides can be used. The operation is described in order of processes.

1. The laser beam 10 is incident from the delay portion 6.
2. Part of the laser beam 10 is coupled with the first optical waveguide 100, as the first excitation light beam 11. The first excitation light beam 11 propagates through the core portion 1 of the first optical waveguide 100 while being totally reflected. At this time, in a region without the optical coupling member 7, the terahertz wave generated from the first optical waveguide 100 cannot be extracted according to Expression 2, and is totally reflected by the first cladding portion 2.
3. The first excitation light beam 11 propagates through the first optical waveguide 100 in the delay portion 6. At this time, other part of the laser beam 10 propagates through the space in the delay portion 6. Since the refractive index of the material of the first optical waveguide 100 differs from the refractive index of the space, the propagation velocity of the first excitation light beam 11 differs from the propagation velocity of the laser beam 10 in the delay portion 6. Consequently, the propagation time of the first excitation light beam 11 in the delay portion 6 becomes longer than that of the laser beam 10, and hence is delayed.
4. Other part of the laser beam 10 that propagates through the space is coupled with the second optical waveguide 200, as the second excitation light beam 12. When the second excitation light beam 12 propagates, the first terahertz wave 8 is generated, and the first terahertz wave 8 propagates through the propagation portion 5. FIG. 1B illustrates the first equiphase surface 13 of the first terahertz wave 8. In the equiphase surface, the phases of the terahertz waves are hypothetically the same. The equiphase surface shown in FIG. 1B is an equiphase surface of a terahertz wave that is generated from a certain generation point in each of the optical waveguides for convenience of the description. Hence, the equiphase surface is illustrated in an arc form. Actually, the terahertz waves are continuously generated in the optical waveguide, and the equiphase surfaces of these terahertz waves are substantially aligned with each other, and hence a conical equiphase surface is formed. An angle in a direction in which the generator of the cone extends is the radiation angle $\theta_5$ of the equiphase surface.
5. At a position directly below the optical coupling member 7, the second terahertz wave 9 is generated from the first excitation light beam 11 that propagates through the first optical waveguide 100, and the second terahertz wave 9 propagates through the optical coupling member 7. FIG. 1B illustrates the second equiphase surface 14 of the second terahertz wave 9 as the result of the propagation.
6. The first terahertz wave 8 reaches the first optical waveguide 100. At this time, since the delay portion 6 and the propagation portion 5 are present, a time at which the first terahertz wave 8 reaches the generation position of the second terahertz wave 9 is substantially aligned with (substantially equivalent to) a time at which the second terahertz wave 9 is generated at the generation position. Consequently, the first equiphase surface 13 of the first terahertz wave 8 is substantially aligned with the second equiphase surface 14 of the second terahertz wave 9. The intensities of the terahertz waves extracted from the optical coupling member 7 are increased. In other words, the phase patching condition of the first terahertz wave 8 and the second terahertz wave 9 is satisfied by adjusting the timings at which the terahertz waves are generated. Consequently, the terahertz waves generated from the plurality of positions can be aligned with each other and extracted. The terahertz waves with high intensities can be generated.

This example uses the parallel light beam as the laser beam 10. In this case, since part of the laser beam 10 is used as the excitation light beam, the use efficiency of the laser beam 10 is slightly decreased. This can be addressed by decreasing the thickness of the propagation portion 5 and stacking more optical waveguides in the irradiation region of the laser beam 10. Here, a ratio of a cross-sectional area of the core portion of the optical waveguide to the beam diameter of the laser beam 10 is defined as use efficiency. For example, in this example, if the beam diameter of the laser beam 10 is 1.56 mm, regarding the cross-sectional area of the core portion 1 that forms the optical waveguide, the use efficiency is lower than about 0.002%. By determining the thickness of the propagation portion 5 to 5 μm, and stacking 150 optical waveguides, the use efficiency of the laser beam 10 is increased to lower than about 0.3%. Also, by expanding the width of the core portion 1 to a region that accommodates the beam diameter of the laser beam 10, and forming the optical waveguide into a slab, the use efficiency is increased. For example, by determining the width of the core portion 1 to 2.00 mm, and stacking 150 optical waveguides, the use efficiency of the laser beam is increased to about 40% to 50%.

EXAMPLE 2

Example 2 of the present invention will be described. This example is a modification of Example 1. Specifically, Example 2 is an example in which a plurality of optical waveguides that generate terahertz waves are arranged in the direction of the normal to the longitudinal direction of the optical waveguides (the direction B in FIG. 1A). Description common to the description provided above will be omitted.

FIG. 1A shows an example in which two rows of optical waveguides are arranged in the direction of the normal. The minimum interval between the optical waveguides is about ($1/10$)λ to ($1/20$)λ with respect to the equivalent wavelength λ of the terahertz wave in the propagation portion 5 with the highest frequency from among frequency components of the terahertz waves desired to be extracted. For example, when the beam diameter of the laser beam 10 is 1.56 mm, the interval between the optical waveguides is 5 μm, and the optical waveguides are arrayed in 150 rows, the light use efficiency becomes lower than about 20%. Also, by forming the array, the generation region of the terahertz waves can be expanded. In this way, by forming the array of the generating elements according to the example of the present invention with a decreased loss for terahertz waves, terahertz waves with high intensities can be collectively generated from a wide region.

Second Embodiment

Figure 2A:
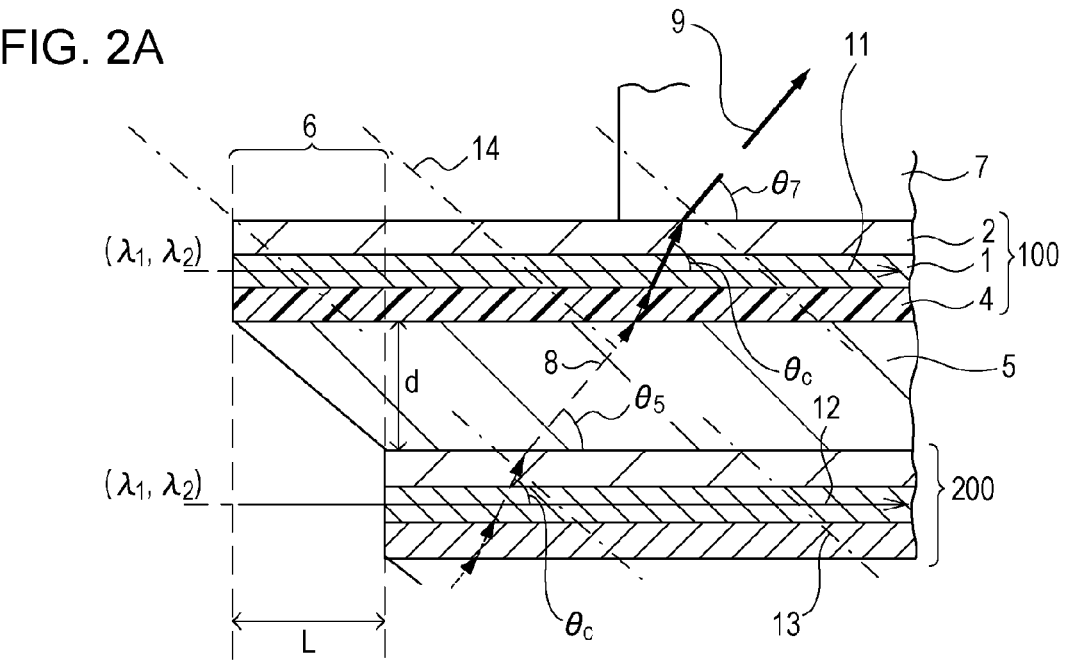
FIG. 2A is a cross-sectional view explaining a terahertz-wave generating element according to another embodiment.
Figure 2B:
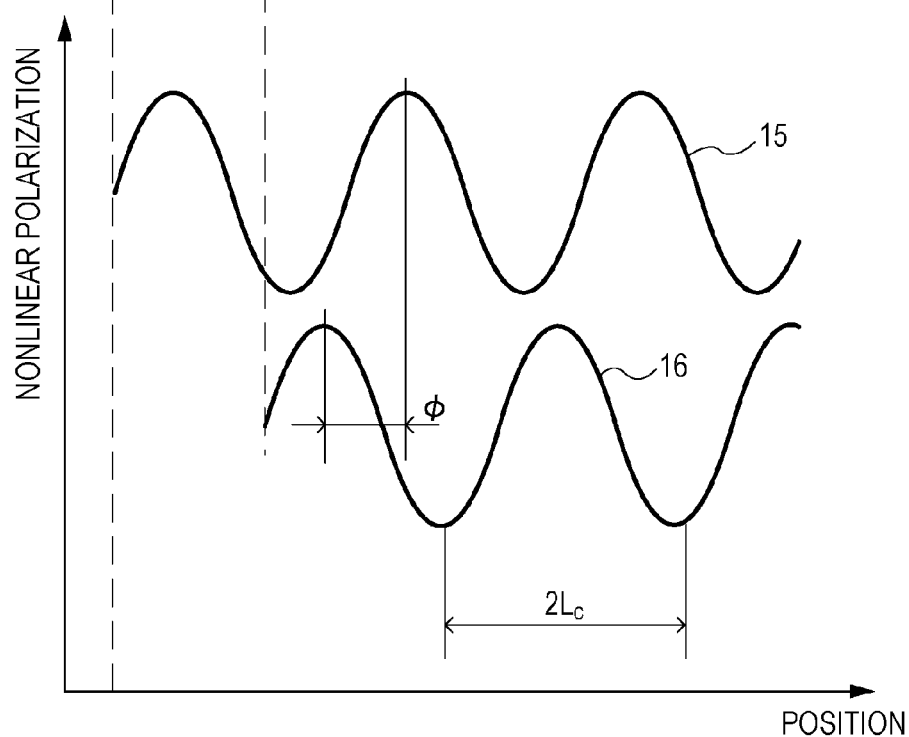
FIG. 2B is an illustration showing nonlinear polarization at each of positions of the terahertz-wave generating element.

A second embodiment of the present invention for terahertz-wave generating element and device etc. will be described. Description common to the description provided above will be omitted. This embodiment is a modification of the first embodiment. Specifically, the terahertz-wave generating element of this embodiment relates to an element that generates a continuous wave. FIGS. 2A and 2B are configuration diagrams of the generating element of this embodiment. FIG. 2A is a cross-sectional view of a portion passing through the center of the core portion 1 in the longitudinal direction of the optical waveguides. FIG. 2B is an illustration showing nonlinear polarization by the first excitation light beam 11 and the second excitation light beam 12 at respective positions of the generating element. Here, nonlinear polarization at the first optical waveguide 100 is named first nonlinear polarization 15. Also, nonlinear polarization at the second optical waveguide 200 is named second nonlinear polarization 16.

Similarly to the element of the first embodiment, the terahertz-wave generating element shown in FIG. 2A has a configuration in which the first optical waveguide 100 and the second optical waveguide 200 are arranged with the propagation portion 5 interposed therebetween. The generating element of the second embodiment differs from the generating element of the first embodiment in that the laser beam 10 of the first embodiment uses the pulsed light beam whereas the laser beam 10 of this embodiment uses two continuous light beams with wavelengths $\lambda_1$ and $\lambda_2$. Also, the methods of determining the thickness d of the propagation portion 5 and the distance L of the delay portion 6 are different, depending on whether the excitation light beam is the pulsed light beam or the continuous light beam. More specifically, if the pulsed light beam is used, the terahertz waves are generated from a single position of the optical waveguide at a time, and if the continuous light beam is used, the terahertz waves are generated from a plurality of positions.

In FIG. 2B, $2L_c$ is a period of nonlinear polarization. The period $2L_c$ of the nonlinear polarization can be expressed as follows:

$$2L_c = \lambda_1 \lambda_2 / (n_1 \lambda_2 - n_2 \lambda_1) \quad (4),$$

where $\lambda_1$ and $\lambda_2$ are wavelengths of two irradiated continuous light beams, and $n_1$ and $n_2$ are refractive indices of the light beams with the wavelength $\lambda_1$ and the wavelength $\lambda_2$ in the optical waveguides. The phases of the terahertz waves generated from the optical waveguides become equivalent every period $2L_c$, and hence form equiphase surfaces. Here, it is assumed that an equiphase surface of the first terahertz wave 8 generated from the second optical waveguide 200 is a first equiphase surface 13. Also, it is assumed that an equiphase surface of the second terahertz wave 9 generated from the first optical waveguide 100 is a second equiphase surface 14. If the wavelength of the terahertz wave generated from the optical waveguide is $\lambda_{THz}$, the radiation angle $\theta_c$ of the terahertz wave can be expressed as follows:

$$\cos \theta_c = (\lambda_{THz} / n_{THz}) / 2L_c \quad (5)$$

where $n_{THz}$ is a refractive index for the terahertz wave in the crystal. If $n_1$ is apparently equivalent to $n_2$, the radiation angle $\theta_c$ is approximated to Expression 1.

In FIG. 2B, $\phi$ is a phase difference between the first nonlinear polarization 15 and the second nonlinear polarization 16. In this embodiment, the phase difference $\phi$ is adjusted by the thickness d of the propagation portion 5 and the distance L of the delay portion 6, and the first equiphase surface 13 is substantially aligned with the second equiphase surface 14. To align the phase surfaces, at least the first terahertz wave 8 generated at the second optical waveguide 200 has to reach the first optical waveguide 100 in the same phase. Accordingly, when the thickness d of the propagation portion 5 is defined, the distance L of the delay portion 6 is defined by Expression 3. With this configuration, the phase matching condition between the first terahertz wave 8 and the second terahertz wave 9 can be satisfied by adjusting the phase difference $\phi$ by the delay portion 6. Consequently, the terahertz waves generated from the plurality of positions can be aligned with each other and extracted. The terahertz waves with high intensities can be generated.

EXAMPLE 3

This example describes an element and a device etc. corresponding to the second embodiment. Description common to the description provided above will be omitted. In this example, two continuous waves with wavelengths of 1.550 µm and 1.558 µm are used as the laser beam 10. Other element configuration is similar to that of Example 1.

When the laser beam 10 is incident on the optical waveguide as the excitation light beam, the period $2L_c$ of the nonlinear polarization distributed in the first optical waveguide 100 and the second optical waveguide 200 is about 144 µm according to Expression 4. At this time, the radiation angle $\theta_c$ of the terahertz wave with respect to the propagation direction of the excitation light beam in the optical waveguide is about 65.6 degrees according to Expression 1. The radiation angle $\theta_S$ of the terahertz wave that propagates through the propagation portion 5 is about 48.8 degrees according to Expression 2. It is assumed that the thickness d of the propagation portion 5 is 50 µm. At this time, the distance L of the delay portion 6 becomes about 57 µm according to Expression 3. The wavelength $\lambda_{THz}$ of the terahertz wave radiated with the above-described configuration becomes about 300 µm according to Expression 5, and a terahertz wave around 1 THz is generated.

Third Embodiment

Figure 4:
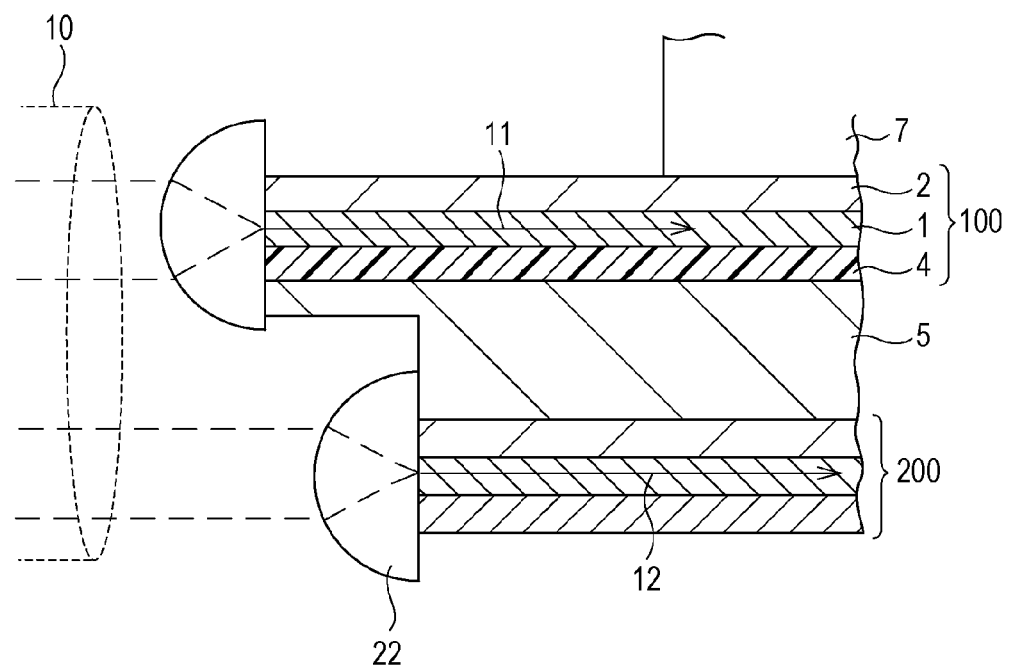
FIG. 4 is an illustration explaining a configuration example of coupling portions with excitation light beams.

This embodiment is a modification of the first and second embodiments. Specifically, the incidence method of the laser beam 10 is different. Description common to the description provided above will be omitted. FIG. 4 illustrates a configuration of an element of this embodiment. The element in FIG. 4 differs from the above-described elements in that, when the laser beam 10 is incident on the element, the laser beam 10 passes through a light condensing member 22 provided at and end surface of the element. The light condensing member 22 may be, for example, a microlens or a fly-eye lens. In this case, the light condensing member 22 is bonded to an end surface portion of each optical waveguide by an optical adhesive. Alternatively, the shape of the end surface of the optical waveguide may have a lens-like shape.

With this embodiment, the laser beam 10 that is subject to optical vignetting by the end surface of the element can be used as the excitation light beam. Accordingly, with element of this embodiment, and with the device using the element of this embodiment, the use efficiency of the laser beam 10 can be further increased.

Fourth Embodiment

Figure 3A:
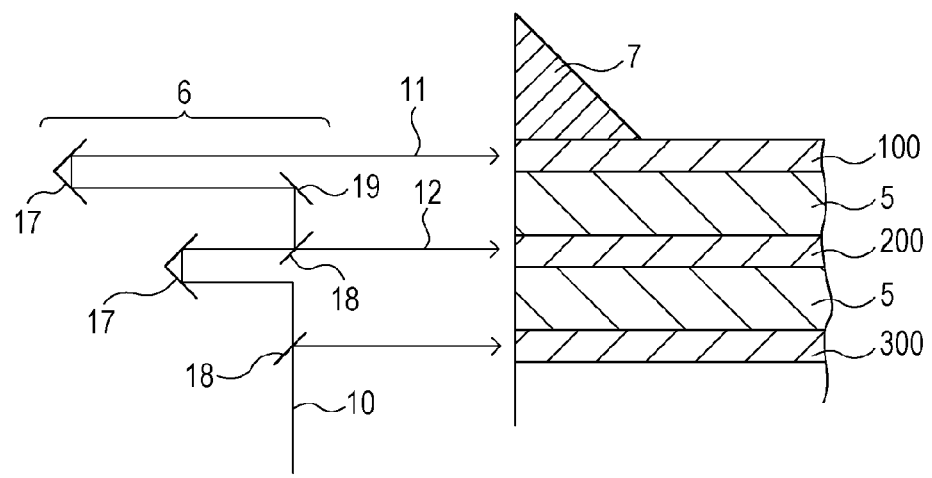
FIG. 3A is an illustration explaining a configuration example of a delay portion.
Figure 3B:
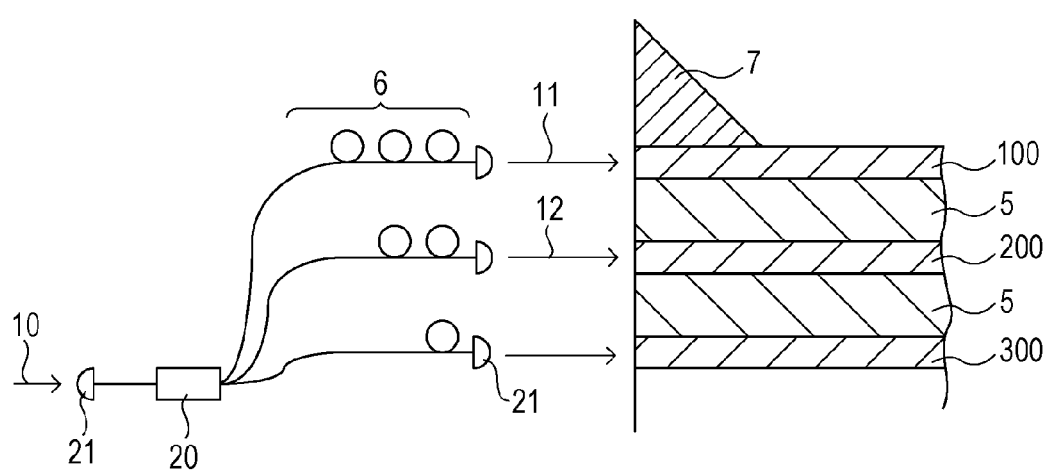
FIG. 3B is an illustration explaining a configuration example of a delay portion.

This embodiment is a modification of the above-described embodiments. Specifically, the configuration of the delay portion 6 is different. Description common to the description provided above will be omitted. FIGS. 3A and 3B are configuration diagrams of devices of this embodiment. In this embodiment, the delay portion 6 is partly or entirely provided outside the element. FIGS. 3A and 3B illustrate examples in which the entire delay portions 6 are provided outside the elements. However, the arrangement is not limited thereto, and a delay portion may be additionally provided outside the element configuration according to any of the above-described embodiments.

FIG. 3A illustrates an example that implements the delay portion 6 by using a difference between optical-path lengths of excitation light beams that are incident on respective optical waveguides. FIG. 3B illustrates an example that provides a difference between optical-path lengths by using lengths of optical fibers through which excitation light beams propagate. Referring to FIGS. 3A and 3B, each device includes two propagation portions 5 and three optical waveguides 100, 200, and 300 arranged with the propagation portions 5 interposed among these optical waveguides 100 to 300. However, as described above, the number of optical waveguides is not limited to that number. End surfaces of these optical waveguides are aligned in a stacking direction of the optical waveguides. Also, an optical coupling member 7 slightly differs from that of the above-described embodiments, and is arranged at an end surface portion of the optical waveguides.

The delay portion 6 in FIG. 3A is provided outside the element. For example, the delay portion 6 includes a folding optical system 17, an optical splitter 18, and an optical reflector 19 (mirror). The folding optical system 17 includes, for example, a linear-motion stage and a retroreflector provided on the linear-motion stage. By adjusting the position of the linear-motion stage in a direction of a light beam that is incident on the folding optical system 17, an optical-path length of an excitation light beam that is incident on each optical waveguide is adjusted. The optical splitter 18 distributes a laser beam 10 into a transmitted light beam and a reflected light beam. In this embodiment, the reflected light beam is used as an excitation light beam. The optical reflector 19 is, for example, a mirror, and is inserted properly depending on the device configuration to adjust the optical path.

The delay portion 6 in FIG. 3B is provided outside the element, and includes a beam coupling member 21 that couples a light beam with a fiber, and a beam splitter 20 that splits a laser beam 10 propagating through the fiber into a plurality of fibers. By adjusting the lengths of the fibers split by the beam splitter 20, optical-path lengths for excitation light beams incident on the respective optical waveguides are adjusted. When the fibers are used, to cause the excitation light beam to be incident on the element, the fibers may be directly fused without the beam coupling member 21. As described above, for optical-path lengths of optical paths in which an output light beam from a light source is split into the first excitation light beam and the second excitation light beam etc., and reaches an output side of the delay portion, the delay portion of this embodiment causes the optical-path length of the optical path through which the first excitation light beam propagates to be larger than the optical-path length of the optical path through which the second excitation light beam etc. propagates.

In this embodiment, the delay portion 6 adjusts the timing and the phase difference $\phi$ of the excitation light beam incident on the element. With this device, the timings and phase difference $\phi$ of the first excitation light beam 11 and the second excitation light beam 12 incident on the terahertz-wave generating element can be adjusted at the outside of the device. Accordingly, the positions of a first equiphase surface 13 and a second equiphase surface 14 can be adjusted at the outside of the device. Robustness of the device is improved, and stability of the device is increased. Also, by combining this element with any of the elements according to the above-described embodiments, the combined configuration can handle variation in equiphase surfaces due to fabrication errors and changes in characteristics of materials. Hence, terahertz waves can be reliably generated. Also, with the above-described embodiments, the excitation light beam propagating through the delay portion 6 provided in the element does not make contribution to the generation of the terahertz wave. In contrast, with this embodiment, the terahertz wave can be extracted from a position near the end surface of the optical waveguide, the use efficiency of the excitation light beam is increased.

Fifth Embodiment

This embodiment provides a configuration example of a device, such as a measuring device using the above-described generating device or element. Specifically, this embodiment relates to a configuration example of an imaging apparatus. Description common to the description provided above will be omitted. FIG. 5 is a configuration example of a tomographic imaging apparatus based on a terahertz time-domain spectroscopic system (THz-TDS) using the generating device or element as a terahertz-wave generating element.

The apparatus in FIG. 5 basically includes a generating element 501 which is described above, a laser source 503 which is a light source that emits a light beam, and a detector 502 that detects a terahertz wave. Also, the apparatus includes a delay optical system 505 that adjusts an optical-path length of a laser beam that is incident on the detector 502, to detect a time waveform from the detector 502. Further, the apparatus includes a detecting unit 506 that monitors an output of the detector 502 and a change in optical-path length of the delay optical system 505, which serves as a delay adjuster, and constructs a time waveform. In the tomographic imaging apparatus, the time waveform of the terahertz wave corresponds to depth-position information for the inside of an imaging object. A sample stage 508 is a stage that holds an imaging object. The sample stage 508 can be moved in a planar direction with respect to an incidence direction of the terahertz wave. An image forming unit 507 causes position information of the sample stage 508 to correspond to the time waveform of the terahertz wave, and constructs a three-dimensional image. The delay adjuster is not limited to the delay optical system and may be any configuration as long as the delay adjuster can adjust a delay time between a timing at which the generating element generates the terahertz wave and a timing at which the detector detects the terahertz wave.

A laser beam 10 which is one light, and a laser beam 1000 which is other light are acquired from the laser source 503 through two fibers of a splitter 504. A femtosecond laser with a center wavelength of 1.55 µm, a pulse width of 20 fs, and a repetition frequency of 50 MHz is typically used. Alternatively, the wavelength may be in a band around 1.06 µm. The pulse width and repetition frequency do not have to be the values described above. When a continuous light beam is used, the laser source 503 is a semiconductor laser. When a femtosecond laser is used as the laser source 503, fibers at the output stage may include a highly nonlinear fiber for higher-order soliton compression at the final stage. Also, a dispersion fiber that performs pre-chirping for compensating dispersion in optical elements located before the generating element 501 that generates the terahertz wave and before the detector 502 and in the elements may be included. Also, these fibers are desirably polarization maintaining fibers. A detection method by the detector 502 may be a method of detecting electric current corresponding to the field intensity of the terahertz wave based on a change in photoconductivity during irradiation with the laser beam 1000. Also, there are a method of detecting an electric field by using an electrooptic effect and a method of detecting a magnetic field by using a magnetooptic effect. A photoconductive element may be applied to the method of detecting the electric current based on the change in photoconductivity.

Particularly in this embodiment, two sensors for positioning of the generating element 501 are provided. Specifically, a first position sensor 509a is provided. The first position sensor 509a detects a reflected light beam 10b that is reflected from an interface (end surface) between the first optical waveguide 100 and the second optical waveguide 200 from among the excitation light beams that is incident on the optical waveguides of the generating element 501. Also, a second position sensor 509b is provided. The second position sensor 509b detects a transmitted light beam 10a that is transmitted through the first optical waveguide 100 and the second optical waveguide 200. These sensors are formed of, for example, quadrant photodiodes. A position detecting unit 510 monitors the outputs of the sensors. The generating element 501 can be accurately positioned by adjusting the position of the generating element 501 such that the two position sensors receive light beams in a predetermined manner.

The operation of this apparatus will be described. The laser source 503 outputs the two laser beams 10 and 1000. The laser beam 10 is incident on the generating element 501, and the terahertz wave 9 is output. At this time, the generating element 501 is accurately positioned by using the laser beam 10, which is actually used. The generated terahertz wave 9 is irradiated on a sample (not shown) held by the sample stage 508, through two parabolic mirrors 513a and 513b and a beam splitter 511. The beam splitter 511 may use, for example, high-resistance silicon. The terahertz wave 9 irradiated on the sample is reflected by the sample. Then, the terahertz wave 9 is incident on the detector 502 through the two parabolic mirrors 513b and 513c and the beam splitter 511.

The terahertz wave incident on the detector 502 is detected by using the laser beam 1000. The laser beam 1000 is irradiated on the detector 502 through two mirrors 512a and 512b and the delay optical system 505. The delay optical system 505 adjusts the propagation length of the laser beam 1000 to change a propagation delay time of the laser beam 1000 relative to the laser beam 10. The detecting unit 506 references the output of the detector 502 and the adjustment amount of the delay optical system 505, and constructs a waveform of the reflected terahertz wave reflected from the sample. The image forming unit 507 adjusts the position of the sample stage 508. The image forming unit 507 causes the position information of the sample stage to correspond to the time waveform constructed by the detecting unit 506, and acquires a tomographic image relating to the sample.

The apparatus of this embodiment positions the terahertz-wave generating device or element by directly using the excitation light beam that is actually used for the generation of the terahertz wave. Accordingly, workability for alignment of the excitation light beam is increased. Also, by using the generating device or element with an enhanced output of the terahertz wave, which is a feature of this embodiment of the present invention, penetrating power of the terahertz wave into the sample is increased, and information of a deeper portion of the sample can be acquired. Further, since the output of the terahertz wave is increased, the S/N ratio of a signal can be increased, and acquisition time of a signal can be decreased. In this embodiment, the tomographic imaging apparatus is described. However, the apparatus form is not limited thereto. For example, an analyzing apparatus or an inspecting apparatus that uses the terahertz time-domain spectroscopic system, monitors a change in time waveform of a terahertz wave from a sample, and analyzes properties of the sample may be applied. Even in this case, the S/N ratio of a signal is increased, and the acquisition time of a signal is decreased.

Sixth Embodiment

In this embodiment, the above-described terahertz-wave generating element is applied to a terahertz-wave detecting element or device etc. The basic element configuration is common to that described above, and hence the description of the common portion is omitted.

Figure 6A:
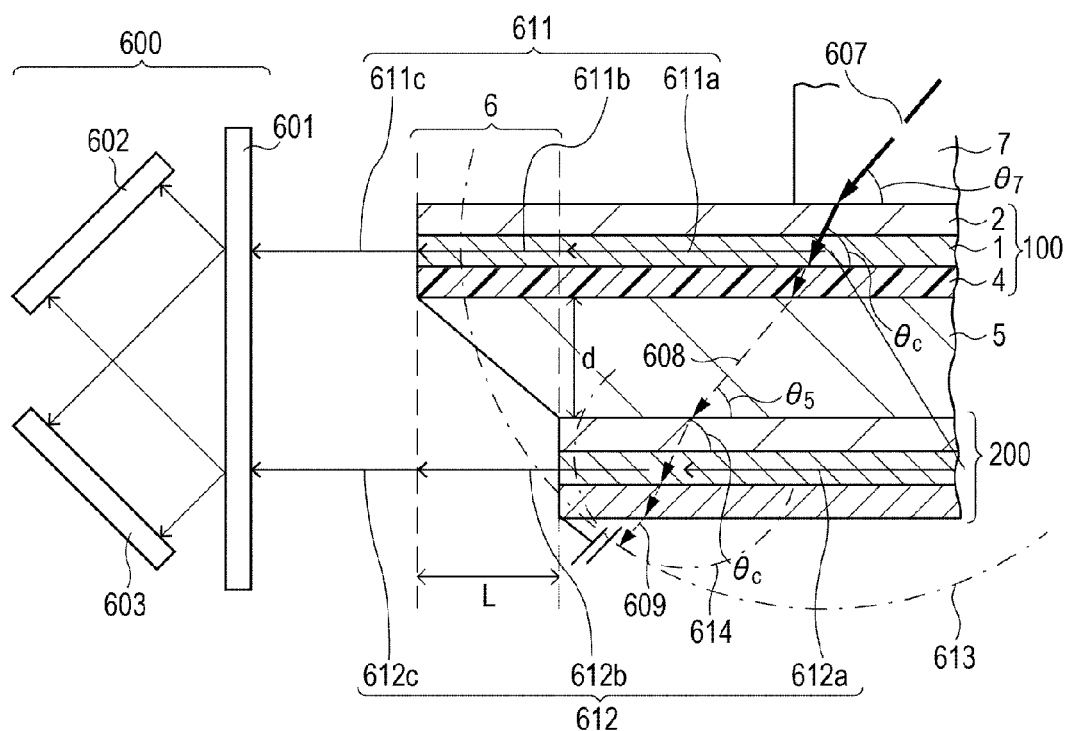
FIG. 6A is an illustration explaining a terahertz-wave generating device according to an embodiment of the present invention.
Figure 6B:
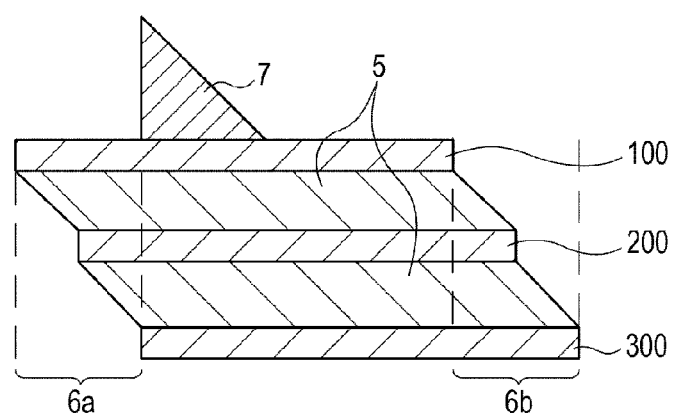
FIG. 6B is an illustration explaining the terahertz-wave generating element according to the embodiment of the present invention.

FIGS. 6A and 6B illustrate configuration examples of a detecting element of this embodiment of the present invention and a detecting device using the detecting element. Referring to FIG. 6A, the detecting element includes a first optical waveguide 100 and a second optical waveguide 200 containing electrooptic crystals. These optical waveguides are arranged with a propagation portion 5 interposed therebetween. In this embodiment, a terahertz wave from a space is coupled with the element by an optical coupling member 7, and thus a terahertz wave 607 is incident. The coupled terahertz wave 607 propagates through the first optical waveguide 100, the propagation portion 5, and the second optical waveguide 200 in that order.

A first excitation light beam 611 that propagates through the first optical waveguide 100 and a second excitation light beam 612 that propagates through the second optical waveguide 200 propagate in a direction opposite to that of any of the above-described embodiments. In the element of this embodiment, the first excitation light beam and the second excitation light beam are emitted to the outside of the element from a delay portion 6 side. The detecting element includes the delay portion 6 that delays the excitation light beam, like the above-described generating element. Specifically, the delay portion 6 delays the first excitation light beam 611 relative to the second excitation light beam 612. Hence, the delay portion 6 shifts the position of an end surface of the first optical waveguide 100 that emits the first excitation light beam 611, with respect to the position of an end surface of the second optical waveguide 200 that emits the second excitation light beam 612, by a predetermined distance L in a propagation direction of the first excitation light beam 611. The value of the distance L can be calculated based on an idea similar to that of the generating element. Specifically, referring to FIG. 6A, an angle $\theta_7$ is used as an incidence angle of the terahertz wave 607, which is coupled with the detecting element and propagates through the optical coupling member 7, onto the optical waveguide. An angle $\theta_c$ is used as an incidence angle of the terahertz wave with respect to the excitation light beam propagating through the optical waveguide. An angle $\theta_5$ is used as an incidence angle of the terahertz wave, which propagates through the propagation portion 5, onto the optical waveguide.

A first terahertz wave 608 passes through the first optical waveguide 100 and is emitted in a direction different from a direction of the first excitation light beam 611. Similarly, a second terahertz wave 609 passes through the second optical waveguide 200 and is emitted in a direction different from a direction of the second excitation light beam 612. At this time, the propagation state of the excitation light beam that propagates through each optical waveguide is changed depending on the electric field of the terahertz wave that propagates through the optical waveguide. Specifically, the propagation state of the excitation light beam is changed depending on the electric field of the terahertz wave that propagates through each optical waveguide when the excitation light beam is instantaneously aligned with the terahertz wave. In other words, electric field information of the terahertz wave at a certain timing is extracted by using the excitation light beam. In this detecting element, the optical waveguides are arranged such that a first equiphase surface 613 of the first terahertz wave 608 and a second equiphase surface 614 of the second terahertz wave 609 are substantially aligned with each other. Referring to FIG. 6A, in fact, since the terahertz wave that propagates through the inside of the detecting element propagates at a certain angle with respect to the propagation direction of the excitation light beam, to substantially align the equiphase surfaces with each other during the measurement with the excitation light beam, a time at which the first excitation light beam 611 reaches the equiphase surface and a time at which the second excitation light beam 612 reaches the equiphase surface have to be previously adjusted. Specifically, referring to FIG. 6A, a second excitation light beam 612a propagates with a delay relative to a first excitation light beam 611a along the equiphase surfaces. For the first excitation light beam 611a and the second excitation light beam 612a, the delay time of a first excitation light beam 611b relative to the second excitation light beam 612b is adjusted. For example, the delay portion 6 adjusts the delay time of the first excitation light beam 611b, for example, to be along a surface (detection surface) of a polarizing element 601 (described later), and the first excitation light beam 611b propagates. If the position of the excitation light beam at an instant moment is plotted, it is found that the resultant line has a certain angle with respect to the propagation direction of the excitation light beam. In this embodiment of the present invention, a surface containing the position of the excitation light beam at this certain instant moment is occasionally expressed as a wavefront of the excitation light beam for convenience of the description. The delay portion 6 adjusts the optical propagation distances of the first excitation light beam 611b and the second excitation light beam 612b, and emits first excitation light beam 611c and second excitation light beam 612c to the space such that the respective excitation light beams reach the detection surface at the same timing. In other words, the delay portion 6 is a portion that adjusts the wavefront shape of the excitation light beam with respect to the propagation direction of the excitation light beam. The delay portion 6 does not have to be provided in the detecting element. For example, a portion configured to spatially adjust the optical length as described with reference to FIG. 3A or 3B may be used as the delay portion 6, to previously adjust the wavefront of the excitation light beam, and to cause the excitation light beam to be incident on the detecting element.

Here, as a portion configured to adjust the delay time between the first excitation light beam 611a and the second excitation light beam 612a, as shown in FIG. 6B, a second delay portion 6b, which is different from a first delay portion 6a may be desirably provided. The first delay portion 6a is the same as the above-described delay portion 6. The second delay portion 6b causes the second excitation light beam 612a to propagate with a delay relative to the first excitation light beam 611a in the propagation direction of the excitation light beam. To provide this, in FIG. 6B, the same structure as that of the first delay portion 6a is arranged point-symmetrically to the detecting element.

A change in propagation state of the excitation light beam is described in detail. When linearly polarized waves of excitation light beams are incident on crystals that form optical waveguides in a manner inclined with respect to the Z-axis (for example, 45 degrees) of the crystals, a phase difference is generated in Z-axis and Y-axis components of electric fields of the excitation light beams emitted from the optical waveguides because of birefringence of the electrooptic crystals. Referring to FIGS. 6A and 6B, the Y-axis is perpendicular to the propagation direction of the excitation light beam and is aligned with the arrangement direction of the waveguides, and the Z-axis is perpendicular to the propagation direction of the excitation light beam and the arrangement direction of the waveguides (perpendicular to the sheet surface). If the phase difference is generated, the excitation light beam emitted to the space propagates in the form of an elliptically polarized wave. The phase difference by natural birefringence varies depending on the type of crystal, incidence polarization direction, and waveguide length. A configuration with zero phase difference may be formed. When a terahertz wave pulse with the principal axis of polarization being the Z-axis by the optical coupling member 7, e.g., a Si prism is incident on the emission surface of the generating element, interaction of the excitation light beam and the terahertz wave that propagate through the optical waveguide can be provided for the entire waveguide in a reverse process of the terahertz wave generation. The interaction is change in polarization state of the propagating excitation light beam because the refractive index of the Z-axis of the optical waveguide is changed by a first-order electrooptic effect (Pockels effect, in particular, an effect of a second-order nonlinear process) that is given to the electrooptic crystal from a terahertz-wave electromagnetic field. Specifically, the phase difference of the Z-axis and Y-axis components in the electric fields of the excitation light beams is changed by dielectric birefringence, and hence the ellipticity of elliptically polarized wave and the direction of the principal axis are changed. By using this, the quantity of a terahertz-wave magnetic field at an instant moment (at a moment when the terahertz wave is aligned with the excitation light beam) can be measured. By adjusting the timing at which the terahertz wave is aligned with the excitation light beam, the time waveform of the terahertz wave can be reconstructed. In the specification of the present invention, the timing at which the terahertz wave is aligned with the excitation light beam may be occasionally expressed as a timing at which the excitation light beam detects the terahertz wave.

As described above, the timing at which the excitation light beam propagates along the equiphase surface of the terahertz wave when the excitation light beam detects the terahertz wave is adjusted. As shown in FIG. 6A, the propagation method of the terahertz wave has a certain angle with respect to the propagation direction of the excitation light beam. Hence, the direction in which the equiphase surfaces are substantially aligned with each other has a certain angle with respect to the propagation direction of the excitation light beam. If the position of the excitation light beam at an instant moment is plotted, the resultant line has a certain angle with respect to the propagation direction of the excitation light beam. In this embodiment of the present invention, a plotted result containing the position of the excitation light beam at this certain instant moment is occasionally expressed as a wavefront of the excitation light beam for convenience of the description. With this expression, the angle of the excitation light beam is, in other words, inclination of the wavefront of the excitation light beam. The delay portion 6 is used to delay the first excitation light beam 611 relative to the second excitation light beam 612 and adjust the inclination of the wavefront of the excitation light beam with respect to the propagation direction of the excitation light beam. The terahertz wave is detected by using the change in propagation state of each excitation light beam. The surface that is provided outside the detecting element according to the embodiment of the present invention for detection of the propagation state is desirably arranged along the inclination of the wavefront of the excitation light beam. In other words, the delay portion 6 may be expressed as a portion that adjusts the inclination of the wavefront of the excitation light beam along the surface for the detection of the propagation state of the excitation light beam. When the surface for the detection of the propagation state of the excitation light beam is aligned with the wavefront of the excitation light beam, the change in propagation state of the excitation light beam output from each optical waveguide that forms the detecting element can be efficiently detected. Accordingly, the change in propagation state of the excitation light beam can be detected with high sensitivity. In other words, by aligning the reach time of each excitation light beam with the position at which the change in propagation state of the excitation light beam is detected, the changes in propagation states are aligned with each other. Consequently, the detection with high sensitivity can be provided.

The arrangement of the optical waveguides is not limited to the above-described arranged, and the optical waveguides may be two-dimensionally arranged with respect to the surface orthogonal to the propagation direction of the excitation light beam like the generating element (FIG. 1A). Also, the form of the optical waveguide may be a slab structure or a ridge structure like the generating element. The form of the excitation light beam to be used may be a pulsed light beam or a continuous light beam like the generating element. Since the terahertz wave is detected in the reverse process of the generating element, the detecting element can have a structure similar to that of the generating element. Also, in this embodiment, the excitation light beam is incident in a forward direction with respect to the propagation direction of the terahertz wave (directions of vector components relating to the propagation direction of the excitation light beam are the same); however, the excitation light beam may be incident in an opposite direction (directions of vector components relating to the propagation direction of the excitation light beam are opposite). In this case, the signal intensity is small because the length by which the terahertz wave matches the excitation light beam is small. However, the signal can be detected. Any of these configurations is selected in accordance with the apparatus configuration.

Next, a configuration example of a terahertz-wave detecting device using the above-described detecting element will be described with reference to FIG. 6A. The detecting device includes a propagation-state detecting unit 600 that detects the above-described propagation state of the excitation light beam. The propagation-state detecting unit 600 includes a polarizing element 601 and photodetectors 602 and 603. In this embodiment of the present invention, the delay portion 6 adjusts the arrival times of the first excitation light beam 611 and the second excitation light beam 622 such that the wavefronts of the excitation light beams are aligned with respect to the polarizing element 601. In this embodiment, the detection surface of the polarizing element 601 is arranged perpendicularly to the propagation direction of the excitation light beam. Hence, the wavefront of the excitation light beam is adjusted to become perpendicular. If a change in propagation state of the excitation light beam is detected with this configuration, the size of the electric-field magnitude of the terahertz wave can be detected. For example, by splitting two polarized light beams of the excitation light beam from each other by a Wollaston polarizing prism as the polarizing element 601, and by detecting outputs of the two photodetectors 602 and 603 by a differential amplifier, the S/N ratio of a signal is increased. However, the differential amplifier does not have to be provided, and a single photodetector (not shown) may detect the intensity while the polarizing element 601 serves as the polarizing plate. Also, a phase compensating plate (for example, $\lambda/4$ plate, not shown) for compensating the natural birefringence may be added between the output end of the detecting element and the polarizing element 601.

With the detecting device using the detecting element according to the embodiment of the present invention, signals of electric field amplitudes of terahertz waves respectively detected from the optical waveguides can be aligned and detected. Thus, detection sensitivity of the terahertz waves can be increased.

Seventh Embodiment

This embodiment is a modification of the above-described detecting elements and detecting devices. Specifically, the delay portion 6a of the detecting element is partly or entirely separated from the detecting element. Description common to the description provided above will be omitted.

Figure 7A:
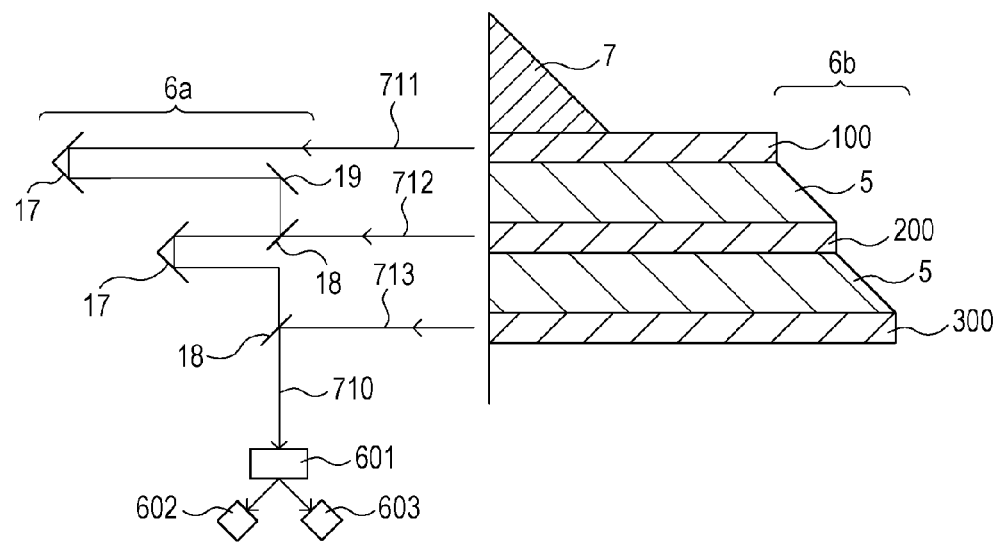
FIG. 7A is an illustration explaining a configuration example of a delay portion.
Figure 7B:
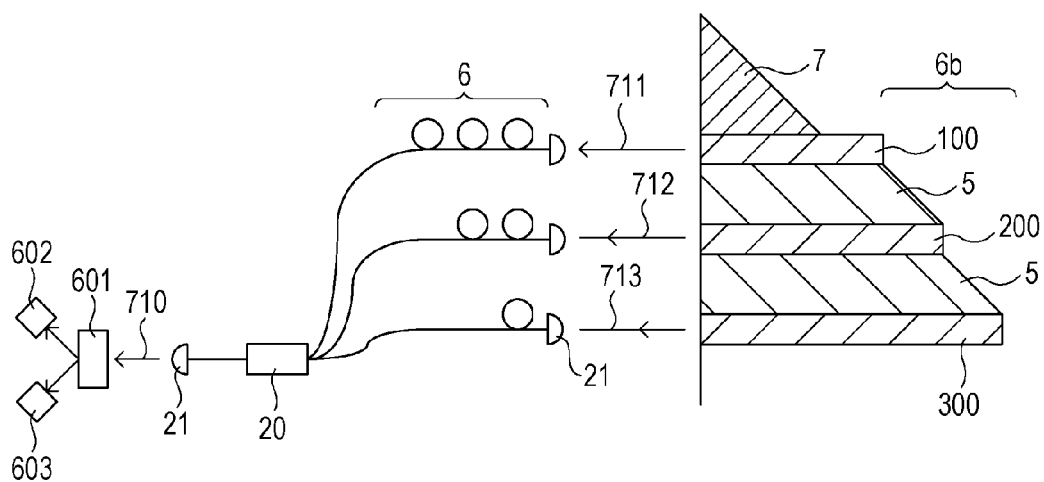
FIG. 7B is an illustration explaining a configuration example of a delay portion.

FIGS. 7A and 7B illustrates configurations of detecting devices. A delay portion 6a has the configuration described in the fourth embodiment. In this embodiment, the second delay portion 6b is stacked in the detecting element, and the delay time of the second excitation light beam relative to the first excitation light beam is previously adjusted. FIG. 7A illustrates an example that implements the delay portion 6a by using a difference between optical-path lengths of excitation light beams that are emitted from respective optical waveguides. FIG. 7B illustrates an example that provides a difference between optical-path lengths by using lengths of optical fibers through which excitation light beams propagate. The propagation-state detecting unit 600, which has been described in the sixth embodiment, is arranged at the output of the delay portion 6a. Excitation light beams 711, 712, and 713 respectively emitted from optical waveguides 100, 200, and 300, which form the detecting element, are combined into the same optical path 710 through the delay portion 6, and the arrival time of the light beams to a polarizing element 601, which forms the propagation-state detecting unit 600, is adjusted. Alternatively, the excitation light beams do not have to be combined and may reach the polarizing element 601 through different optical paths, as long as light beams arrive at the polarizing element 601 at substantially the same timings.

In this embodiment, the delay portion 6a adjusts the timing and phase difference φ of the excitation light beams that are emitted from the element and are incident on the propagation-state detecting unit 600. With such a device, the timings of the excitation light beams 711, 712, and 713, which are emitted from the terahertz-wave detecting element and reach the propagation-state detecting unit 600 can be adjusted at the outside.

Eighth Embodiment

This embodiment provides a modification of the device described in the fifth embodiment. Specifically, the detector 502 of the imaging apparatus shown in FIG. 5 is replaced with the above-descried detecting element and the detecting device using the detecting element. In this case, since the detecting element with the same configuration as that of the generating element 501 can be used, the characteristics of these elements can be the same. Consequently, degradation in signal due to a difference in characteristic (mainly, frequency characteristic) between the elements can be restricted, and detection sensitivity for a terahertz wave reaching a detector is increased. Alternatively, only the detecting element of the configuration according to the embodiment of the present invention may be used. In this case, since a plurality of excitation light beams emitted from a plurality of optical waveguides are aligned with each other and detected, an increase in detection sensitivity can be expected.

Figure 8:
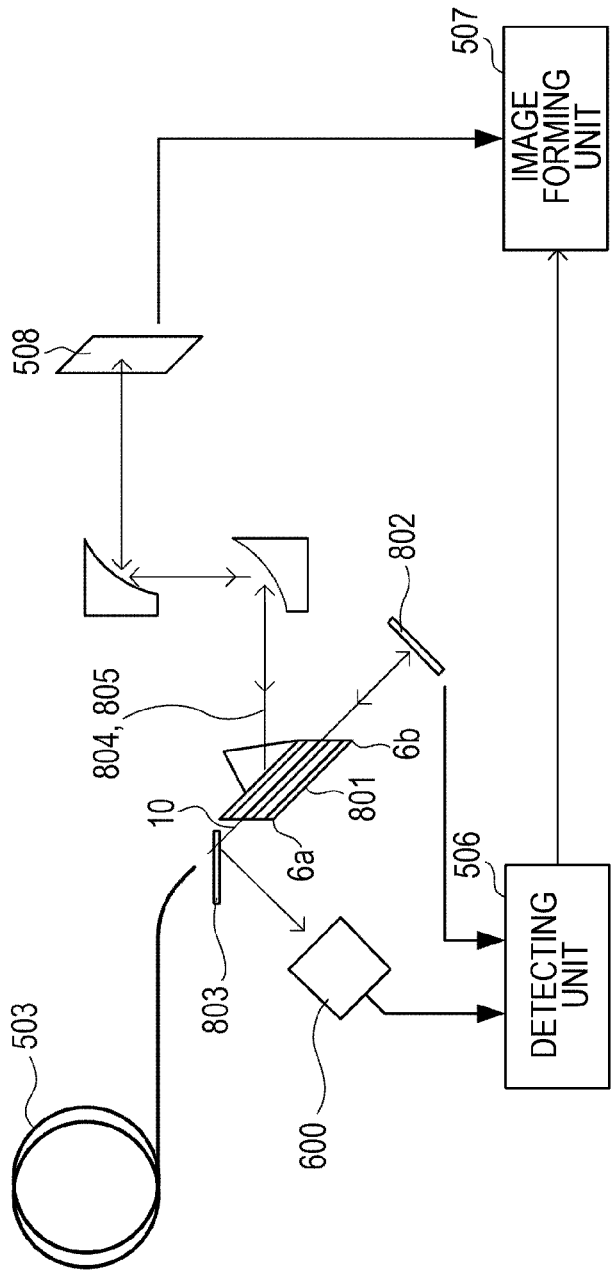
FIG. 8 is an illustration explaining an imaging apparatus according to an embodiment of the present invention.

Also, FIG. 8 illustrates a device configuration in which the element according to the embodiment of the present invention is used for both generation and detection. The device in FIG. 8 uses a generating and detecting element 801 that functions as both the generating element and detecting element described in the embodiments of the present invention. In FIG. 8, the generating and detecting element 801 includes a first delay portion 6a and a second delay portion 6b at both ends of the element. The first delay portion 6a causes the optical-path length of an optical path of a first excitation light beam 11, 611 to be larger than the optical-path length of an optical path of a second excitation light beam 12, 612. Hence, the first excitation light beam 11, 611 is delayed relative to the second excitation light beam 12, 612 and then the excitation light beams propagate through the optical waveguides. The second delay portion 6b causes the optical-path length of the optical path of the second excitation light beam 12, 612 to be larger than the optical-path length of the optical path of the first excitation light beam 11, 611. Hence, the second excitation light beam 12, 612 is delayed relative to the first excitation light beam 11, 611 and then the excitation light beams propagate through the optical waveguides. Also, a delay optical system 802 is arranged at an end surface different from an end surface, on which a laser beam 10 output from a laser source 503 is incident, of the generating and detecting element 801. The delay optical system 802 reflects emitted light beams containing the first and second excitation light beams output from the generating and detecting element 801, along an emission optical path.

Operation is described. The laser beam 10 emitted from the laser source 503 is incident on the generating and detecting element 801 through a beam splitter 803. The laser beam 10 incident on the generating and detecting element 801 actually propagates through the respective optical waveguides as the first excitation light beam 11 and the second excitation light beam 12. In the above description, the wordings, the first excitation light beam and the second excitation light beam, are used for convenience of the description; however, the number of excitation light beams is changed in accordance with the number of optical waveguides through which the excitation light beams are guided. The first excitation light beam 11 propagating through the first delay portion 6a is delayed relative to the second excitation light beam 12 in accordance with an equiphase surface of a terahertz wave. A terahertz wave 804 generated from the generating and detecting element 801 is irradiated on a sample placed on a sample stage 508 through an optical system such as a mirror. A terahertz wave 805 reflected by the sample is incident on the generating and detecting element 801 again through the optical path of the irradiated terahertz wave. The second excitation light beam 12 that propagates through the generating and detecting element 801 is delayed by the second delay portion 6b relative to the first excitation light beam 11 and is emitted from the generating and detecting element 801. At this time, if the delay amount of the first delay portion 6a is the same as the delay amount of the second delay portion 6b (the same optical-path length difference), the delay amount between the excitation light beams emitted from the generating and detecting element 801 is substantially zero. The respective excitation light beams emitted from the generating and detecting element 801 are incident on the delay optical system 802, are folded, and are incident again on the generating and detecting element 801. The time-base position of the terahertz wave that is detected by the excitation light beam is adjusted depending on the folding amount. For the excitation light beams incident on the generating and detecting element 801, the second excitation light beam 612 is delayed by the second delay portion 6b relative to the first excitation light beam 611 and propagates. If the delay amount of the first delay portion 6a is the same as the delay amount of the second delay portion 6b, the respective excitation light beams interact with the terahertz waves at the equiphase surfaces of the terahertz waves propagating through the generating and detecting element 801 when the terahertz waves are detected by the excitation light beams. Consequently, the propagation states of the excitation light beams are changed. For these excitation light beams, the first delay portion 6a adjusts again the delay amount of the first excitation light beam 611 relative to the second excitation light beam 612. The respective excitation light beams emitted from the first delay portion 6a are reflected by the beam splitter 803 and are incident on a propagation-state detecting unit 600. The respective excitation light beams with the delay amounts adjusted by the first delay portion 6a reach the propagation-state detecting unit 600 substantially at the same timings, and the terahertz waves are detected. The detecting unit 506 references the output of the propagation-state detecting unit 600 and the adjustment amount of the delay optical system 802, and constructs the time waveform of the terahertz wave. An image forming unit 507 causes position information of the sample stage 508 to correspond to the time waveform of the terahertz wave and acquires a tomographic image of the sample.

With this configuration, by unitizing elements for generation and detection into an element, the apparatus can be decreased in size. With this tomographic imaging apparatus, the delay portion is stacked in the generating and detecting element. Alternatively, the delay portion may be separately provided (in this embodiment, such a device is also referred to as generating and detecting device).

In this embodiment, the tomographic imaging apparatus is mainly described. However, the apparatus form is not limited thereto. For example, an analyzing apparatus or an inspecting apparatus that uses the terahertz time-domain spectroscopic system (THz-TDS), monitors a change in time waveform of a terahertz wave from a sample, and analyzes properties of the sample may be applied. Even in this case, advantages similar to those of the tomographic imaging apparatus can be expected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-175826 filed Aug. 5, 2010 and No. 2011-152377 filed Jul. 8, 2011, which are hereby incorporated by reference herein in their entirety.

What is claimed is:

1. A terahertz-wave generating device including an optical waveguide containing an electrooptic crystal, the device comprising:
   a first optical waveguide through which a first light beam propagates;
   a second optical waveguide through which a second light beam propagates;
   a propagation portion through which a first terahertz wave propagates, the first terahertz wave being generated from the second optical waveguide in a direction different from a direction of the second light beam; and
   a delay portion arranged at incidence sides of the first and second light beams and configured to delay the first light beam relative to the second light beam,
   wherein the first optical waveguide and the second optical waveguide are arranged with the propagation portion interposed therebetween, and
   wherein a first equiphase surface of the first terahertz wave is substantially aligned with a second equiphase surface of a second terahertz wave that is generated from the first optical waveguide in a direction different from a direction of the first light beam.

2. The terahertz-wave generating device according to claim 1,
   wherein the delay portion has a structure configured to shift a position of an end surface of the second optical waveguide at the incidence side of the second light beam, with respect to a position of an end surface of the first optical waveguide at the incidence side of the first light beam, by a predetermined distance in a propagation direction of the second light beam.

3. The terahertz-wave generating device according to claim 1,
   wherein, for optical-path lengths of optical paths in which a light beam output from a light source is split into the first light beam and the second light beam and the first and second light beams propagate to an output side of the delay portion, the delay portion causes the optical-path length of the optical path through which the first light beam propagates to be optically larger than the optical-path length of the optical path through which the second light beam propagates.

4. The terahertz-wave generating device according to claim 1,
   wherein a core portion of the first optical waveguide is aligned with a core portion of the second optical waveguide in a direction of a propagation path of the terahertz wave from the second optical waveguide to the first optical waveguide, and is arranged in parallel to propagation directions of the respective light beams.

5. The terahertz-wave generating device according to claim 1, further comprising:
   a first position sensor configured to detect a reflected light beam, which is a light beam included in the light beams incident on the respective optical waveguides and is reflected by an interface of the delay portion in a path from the first optical waveguide to the second optical waveguide, and a second position sensor configured to detect a transmitted light beam, which is included in the light beams incident on the respective optical waveguides and is transmitted through the first optical waveguide and the second optical waveguide,
   wherein the terahertz-wave generating device can be positioned by using the first position sensor and the second position sensor.

6. A measuring device using a terahertz time-domain spectroscopic system, the device comprising:
   the terahertz-wave generating device that generates a terahertz wave according to claim 1.

7. A terahertz-wave generating element including an optical waveguide containing an electrooptic crystal, the element comprising:
   a first optical waveguide through which a first light beam propagates;
   a second optical waveguide through which a second light beam propagates;
   a propagation portion through which a first terahertz wave propagates, the first terahertz wave being generated from the second optical waveguide in a direction different from a direction of the second light beam; and
   a delay portion configured to delay the first light beam relative to the second light beam,
   wherein the first optical waveguide and the second optical waveguide are arranged with the propagation portion interposed therebetween,
   wherein the delay portion has a structure configured to shift a position of an end surface of the second optical waveguide at an incidence side of the second light beam, with respect to a position of an end surface of the first optical waveguide at an incidence side of the first light beam, by a predetermined distance in a propagation direction of the second light beam, and
   wherein a first equiphase surface of the first terahertz wave is substantially aligned with a second equiphase surface of a second terahertz wave that is generated from the first optical waveguide in a direction different from a direction of the first light beam.

8. The terahertz-wave generating element according to claim 7,
wherein a plurality of terahertz-wave generating elements are arranged in a direction normal to a longitudinal direction of the first optical waveguide.

9. A measuring device using a terahertz time-domain spectroscopic system, the device comprising:
the terahertz-wave generating element that generates a terahertz wave according to claim 7.

10. A terahertz-wave detecting device including an optical waveguide containing an electrooptic crystal, the device comprising:
a first optical waveguide through which a first light beam propagates;
a second optical waveguide through which a second light beam propagates;
a propagation portion through which a first terahertz wave propagates, the first terahertz wave being emitted from the first optical waveguide in a direction different from a direction of the first light beam;
a delay portion arranged at emission sides of the first and second light beams and configured to delay the first light beam relative to the second light beam; and
a propagation-state detecting unit configured to detect changes in propagation states of the first and second light beams,
wherein the first optical waveguide and the second optical waveguide are arranged with the propagation portion interposed therebetween, and
wherein a first equiphase surface of the first terahertz wave when the first terahertz wave is detected by the first light beam is substantially aligned with a second equiphase surface of a second terahertz wave that is emitted from the second optical waveguide in a direction different from a direction of the second light beam when the second terahertz wave is detected by the second light beam.

11. The terahertz-wave detecting device according to claim 10,
wherein, for optical-path lengths of optical paths of the first light beam and the second light beam from an input side of the delay portion to the propagation-state detecting unit, the delay portion causes the optical-path length of the optical path through which the first light beam propagates to be larger than the optical-path length of the optical path through which the second light beam propagates.

12. A measuring device using a terahertz time-domain spectroscopic system, the device comprising:
the terahertz-wave detecting device that detects a terahertz wave according to claim 10.

13. A terahertz-wave detecting element including an optical waveguide containing an electrooptic crystal, the element comprising:
a first optical waveguide through which a first light beam propagates;
a second optical waveguide through which a second light beam propagates; and
a propagation portion through which a first terahertz wave propagates, the first terahertz wave being emitted from the first optical waveguide in a direction different from a direction of the first light beam,
wherein the first optical waveguide and the second optical waveguide are arranged with the propagation portion interposed therebetween, and
wherein a first equiphase surface of the first terahertz wave when the first terahertz wave is detected by the first light beam is substantially aligned with a second equiphase surface of a second terahertz wave that is emitted from the second optical waveguide in a direction different from a direction of the second light beam when the second terahertz wave is detected by the second light beam.

14. The terahertz-wave detecting element according to claim 13, further comprising:
a delay portion arranged at emission sides of the first and second light beams and configured to delay the first light beam relative to the second light beam,
wherein the delay portion has a structure configured to shift a position of an end surface of the first optical waveguide at the emission side of the first light beam, with respect to a position of an end surface of the second optical waveguide at the emission side of the second light beam, by a predetermined distance in a propagation direction of the first light beam.

15. The terahertz-wave detecting element according to claim 13, further comprising:
a delay portion arranged at incidence sides of the first and second light beams and configured to delay the second light beam relative to the first light beam,
wherein the delay portion has a structure configured to shift a position of an end surface of the first optical waveguide at the incidence side of the first light beam, with respect to a position of an end surface of the second optical waveguide at the incidence side of the second light beam, by a predetermined distance in a propagation direction of the first light beam.

16. The terahertz-wave detecting element according to claim 13,
wherein a plurality of the terahertz-wave detecting elements are arranged in a direction of normal to a longitudinal direction of the first optical waveguide.

17. A measuring device using a terahertz time-domain spectroscopic system, the device comprising:
the terahertz-wave detecting element that detects a terahertz wave according to claim 13.

18. The measuring device using the terahertz time-domain spectroscopic system according to claim 17,
wherein the terahertz-wave detecting element is also used as a terahertz-wave generating element.

19. A method of generating a terahertz wave by using terahertz waves generated from first and second optical waveguides containing electrooptic crystals, the method comprising the steps of:
causing a first light beam to propagate through the first optical waveguide;
causing a second light beam to propagate through the second optical waveguide; and
at a generation position in the first optical waveguide in which a second terahertz wave is generated by the first light beam, aligning a time, at which a first terahertz wave that is generated from the second optical waveguide by the second light beam reaches the generation position, is substantially aligned with a time, at which the second terahertz wave is generated at the generation position, and generating the terahertz waves while a first equiphase surface of the first terahertz wave is substantially aligned with a second equiphase surface of the second terahertz wave,
wherein the equiphase surfaces are substantially aligned by causing the first light beam to propagate with a delay relative to the second light beam, and by causing the first terahertz wave to consume a time before the first terahertz wave reaches the generation position from the second optical waveguide.

20. A method of detecting terahertz waves that are respectively incident on first and second optical waveguides containing electrooptic crystals, by detecting first and second light beams that propagate through the first and second optical waveguides by a detector, the method comprising the steps of:

causing the first light beam to propagate through the first optical waveguide;

causing the second light beam to propagate through the second optical waveguide;

causing the second light beam to propagate with a delay relative to the first light beam such that an equiphase surface of a first terahertz wave emitted from the first optical waveguide when the first terahertz wave is detected by the first light beam is substantially aligned with an equiphase surface of a second terahertz wave that is emitted from the second optical waveguide when the second terahertz wave is detected by the second light beam; and causing the first light beam to propagate with a delay relative to the second light beam such that a time at which the first light beam reaches the detector is substantially the same as a time at which the second light beam reaches the detector.

* * * * *